US007858300B2

(12) United States Patent
Watier et al.

(10) Patent No.: US 7,858,300 B2
(45) Date of Patent: Dec. 28, 2010

(54) METHODS AND COMPOSITIONS TO EVALUATE ANTIBODY TREATMENT RESPONSE

(75) Inventors: Hervé Watier, Ballan-Mire (FR); Guillaume Cartron, Savonniéres (FR); Philippe Colombat, Larcay (FR)

(73) Assignee: Centre Hospitalier Regional et Universitaire de Tours, Cedex Tours (FR)

( * ) Notice: Subject to any disclaimer, the term of this patent is extended or adjusted under 35 U.S.C. 154(b) by 0 days.

(21) Appl. No.: 10/492,183

(22) PCT Filed: Oct. 11, 2002

(86) PCT No.: PCT/EP02/11397

§ 371 (c)(1),
(2), (4) Date: Apr. 9, 2004

(87) PCT Pub. No.: WO03/035904

PCT Pub. Date: May 1, 2003

(65) Prior Publication Data

US 2005/0064417 A1 Mar. 24, 2005

(30) Foreign Application Priority Data

Oct. 19, 2001 (EP) .................... 01402718

(51) Int. Cl.
*C12Q 1/68* (2006.01)
*C07H 21/04* (2006.01)
*A61K 39/395* (2006.01)
*C07K 14/00* (2006.01)
*C12P 19/34* (2006.01)
*G01N 33/53* (2006.01)

(52) U.S. Cl. .................... 435/6; 435/91.2; 435/7.1; 536/24.3; 424/130.1; 530/350

(58) Field of Classification Search .............. None
See application file for complete search history.

(56) References Cited

U.S. PATENT DOCUMENTS

| 5,552,526 | A | * | 9/1996 | Nakamura et al. .......... 530/350 |
| 5,830,652 | A | | 11/1998 | Kimberly et al. |
| 5,866,337 | A | * | 2/1999 | Schon .......................... 435/6 |
| 5,985,561 | A | | 11/1999 | Kimberly et al. |
| 6,294,347 | B1 | | 9/2001 | Peltz et al. |
| 6,444,789 | B1 | | 9/2002 | Luo |
| 6,676,927 | B1 | | 1/2004 | Ravetch |
| 2002/0076702 | A1 | * | 6/2002 | Anand et al. ................... 435/6 |

FOREIGN PATENT DOCUMENTS

| WO | WO 01/12848 | | 2/2001 |
| WO | WO 0112848 | * | 2/2001 |
| WO | WO 03035904 A2 | | 5/2003 |

OTHER PUBLICATIONS

Koene, Harry et al. FCGRIIIAV/F Polymorphism Influences the Binding of IfG by Natural Killer Cell FCGIIIA, Independtly of the FCGIIIA-48L/R/H Phenotype. Aug. 1997. Blood, vol. 90, No. 3 pp. 1109-1114.*
Colombat, Phillippe et al. Rituximab (anti CD20 monoclonal antibody) as single first line therapy for patients with follicular lymphoma with a low tumore burden; clinical and molecular evaluation. Jan. 2001. Blood, vol. 97, No. 1 pp. 101-106.*
Farag, Sherif et al. FCGRIIIA and FCGRIIA polymorhisms do not predict response to rituximab in B-cell chronic lymphocytic leukemia. Feb. 2004. Blood, vol. 103, No. 4 pp. 1472-1474.*
Syvanen, Ann Christine. Accessing genetic variation: genotyping single nucleotide polymoprhisms. 2001. Nature Reviews Genetics. vol. 2, pp. 930-942.*
Maloney, David et al. IDEC-C2B8 9rituximab) anti CD20 monoclonal antibody therapy in patients with relapsed low grade non Hodgkins lymphoma. 1997. Blood vol. 90 pp. 2188-2195.*
Shevchenko, Andrej et al. Mass spectrometric sequencing of proteins from silver stained polyacrylamide gels. 1996. Analytical Chemistry. vol. 68 pp. 850-858.*
Wu, Jianming et al. A novel polymoprhism of FCGR3a (CD16) alters receptor function and predisposes to autoimmune disease. 1997. Journal of Clinical Investigations. vol. 100 pgaes 1059-1070.*
GenBank Accession NM_000569 GI: 10835136 Oct. 17, 2000.*
Colombat, P., et al. "Rituximab (anti-CD-20 monoclonal antibody) as single first-line therapy for patients with follicular lymphoma with a low tumor burden: clinical and molecular evaluation" *Blood* (2001), 97(1)101-106.
Caltz, R., et al. "Association of Fcγ RIIIA-158F allele with rheumatoid arthritis" Arthritis and Rheumatism, Lippincott, Philadephia, PA, U.S., vol. 42, Sep. 1999, p. S245.
Leppers-Van E Straat, F.G.J., et al. "A novel PCR-based method for direct Fcβ receptor IIIa (CD16) allotyping" *J. Immunol. Methods* (2000), 242:127-132.
Cartron, G et al. (2002) "Therapeutic activity of humanized anti-CD20 monoclonal antibody and polymorphism in IgG Fc receptor FcγRIIIa gene" Blood 99(3):754-758.
Cartron, G. et al. (2004) "From the bench to the bedside: Ways to improve rituximab efficiency" *Blood* First Edition Paper, prepublished on-line Jun. 29, 2004; DOI 10.1182/blood-2004-03-1110.

(Continued)

*Primary Examiner*—Stephen Kapushoc
*Assistant Examiner*—Amanda Shaw
(74) *Attorney, Agent, or Firm*—McCarter & English, LLP

(57) ABSTRACT

The present invention relates to methods and compositions to evaluate or assess the response of a subject to particular therapeutic treatment. More particularly, the invention provides methods to determine the response of subjects, or to adapt the treatment protocol of subjects treated with therapeutic antibodies. The invention is based on a determination of the FCGR3A genotype of a subject. The invention can be used for patients with malignancies, particularly lymphoma, and is suited to select best responders and/or adjust treatment condition or protocol for low responders.

24 Claims, 11 Drawing Sheets

OTHER PUBLICATIONS

Figure 1:
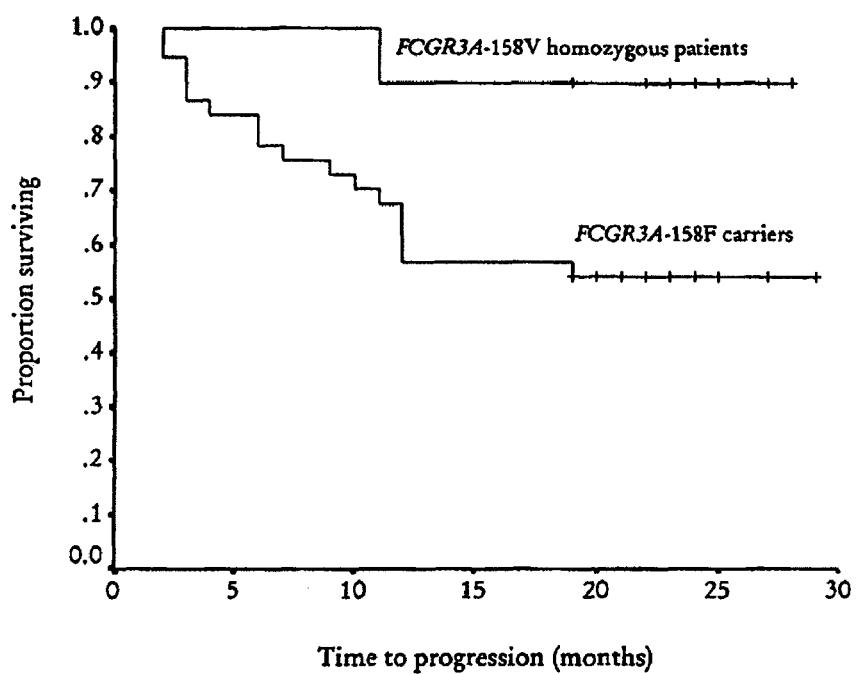

Cheson, B.D. et al. (1999) "Report of an international workshop to standardize response criteria for non-Hodgkin's lymphomas" *J. Clin. Oncol.* 17(4):1244-1257.

Clynes, R. et al. (1998) "Fc receptors are required in passive and active immunity to melanoma" *Proc. Natl. Acad. Sci. U.S.A.* 95:652-656.

Clynes, R.A. et al. (2000) "Inhibitory Fc receptors modulate in vivo cytotoxicity against tumor targets" *Nature Medicine* 6(4):443-446.

Farag, S.S. et al. (2004) Fcγ and FcγRIIa polymorphisms do not predict response to rituximab inB-cell chronic lymphocytic leukemia. *Blood* 103(4):1472-1474.

de Haas, M. et al.(1996) "A triallelic Fcγreceptor type IIIA polymorphism influences the binding of human IgG by NK cell Fcγ RIIIa" *J. Immunol.* 156:3948-3955.

Jiang, X.M. et al. (1996) "Rapid detection of the FcγRIIA-H/R 131 ligand-binding polymorphism using an allele-specific restriction enzyme digestion (ASRED)" *J. Immunol Methods* 199:55-59.

Kaplan, E. and P. Meier. (1958) "Nonparametric estimation from incomplete observations" *J. Am. Stat. Assoc.* 53:457-481.

Kennedy, A.D. et al. (2004) "Rituximab infusion promotes rapid complement depletion and acute CD20 loss in chronic lymphocytic leukemia" *J. Immunol.* 172:3280-3288.

Koene, H.R. et al. (1997) "FcγRIIIa-158V/F polymorphism influences the binding of IgG by natural killer cell FcγRIIIa, independently of the FcγRIIIa-48L/R/H phenotype" *Blood* 90(3):1109-1114.

Lehrnbecher, T. et al. (1999) "Variant genotypes of the low-affinity Fcγ receptors in two control populations and a review of low-affinity Fcγ receptor polymorphisms in control and disease populations" *Blood* 94(12):4220-4232.

Lin, T.S. et al. (2004) "FCGR3A and FCGR3A polymorphisms may not correlate with response to alemtuzumab (Campath-1H) in chronic lymphocytic leukemia (CLL)" *Blood* First Edition Paper, prepublished on-line Jun. 24, 2004; DOI 10.1182/blood-2004-02-0651.

Peltz, G.A. et al. (1989) Human FcγRIII: Cloning, expression, and identification of the chromosomal locus of two Fc receptors for IgG. *Proc. Natl. Acad. Sci. U.S.A.* 86:1013-1017.

Ravetch, J.V. (2002) "A full complement of receptors n immune complex disease" *J. Clin Invest.* 110:1759-1761.

Schnackenberg, L. et al. (1997) Linkage disequilibria between Duffy blood groups, Fcγ IIa and FcγIIIb allotypes. *Exp. Clin Immunogenet.* 14:235-242.

Shields, R. et al. (2001) "High resolution mapping of the binding site on human IgG1 for FcγRI, FcγRII, FcγRIII, and FcRn and design of IgG1 variants with improved binding to the Fcγ R*" *J. Biol. Chem.* 276(9):6591-6604.

Vance, B. et al. (1993) "Binding of monomeric human IgG defines an expression polymorphism of FCγRIII on large granular lymphocyte/natural killer cells" *J. Immunol.* 151:6429-6439.

Wu, J. et al. (1997) "A novel polymorphism of FCγRIIIa (CD16) alters receptor function and predisposes to autoimmune disease" *J. Clin. Invest.* 100:1059-1070.

Kumpel, B.M. et al. "Clearance of red cells by monoclonal IgG3 anti-D in vivo is effected by the VF polymorphism of FcγRIIIa (CD16)" *Clin. Exp. Immunol.*, 2003, vol. 132, pp. 81-86.

Preithner, S. et al. "High concentrations of therapeutic IgG antibodies are needed to compensate for inhibition of antibody-dependent cellular cytotoxicity by excess endogenous immunoglobulin G" *Mol. Immunol.*, Mar. 2006, vol. 43, No. 8, pp. 1183-1193.

Anderson et al. (1997) "Targeting Cytotoxic Immunotherapy", Biochem. Soc. Trans. 25: 705-708.

Aster RH, (2005) "Drug-induced immune cytopenias" Toxicology, 209:149-153.

Bowles and Weiner, (2005) "CD16 polymorphisms and NK activation induced by monoclonal antibody-coated target cells", J. Immunol. Methods 304: 88-99.

Carcao, M. et al. (2003) "Fcγ Receptor IIa and IIIa polymorphisms in childhood immune thrombocytopenic purpura", British Journal of Haematology, pp. 135-141, vol. 120, No. 1.

Carlotti et al. (2007) "FcγRIIIA and FcγRIIA polymorphisms do not predict clinical outcome of follicular non-Hodgkin's lymphoma patients treated with sequential CHOP and rituximab", Haematologica 92: 1127-1130.

Citizen Petition of Genentech (2008) "Require all in Vitro Diagnostic Tests Intended for use in Drug or Biologic Therapeutic Decision Making be Held to the Same Scientific and Regulatory Standards", Docket FDA-2008-P-0638.

Dall'Ozzo et al., (2003) "Rapid single-step FCGR3A genotyping based on SYBR Green I fluorescence in real-time multiplex allele-specific PCR" J Immunol Methods, 277:185-192.

Foster et al. (2002) "FCGR3A V/F polymorphism does not predict response to Herceptin (H) monotherapy" ASCO Annual Meeting Abstract No. A227.

Fujimoto, T. et al. (2001) "Involvement of Fcγ receptor polymorphism in the therapeutic response of idiopthic thrombocytopenic purpura", British Journal of Haematology, vol. 115, No. 1, pp. 125-130.

Ghielmini et al.(2005) "Single agent rituximab in patients with follicular or mantle cell lymphoma: clinical and biological factors that are predictive of response and event-free survival as well as the effect of rituximab on the immune system: a study of the Swiss Group for Clinical Cancer Research (SAKK)", Annals of Oncology 16:1675-1682.

Greinacher et al. (2001) "Drug-Induced and Drug-Dependent Immune Thrombocytopenias" Rev Clin Exp Hematol. vol. 5(3): 166-200.

Gruel, Y. et al. (2004) "The homozygous FcγRIIIa-158V genotype is a risk factor for heparin-induced thrombocytopenia in patients with antibodies to heparin-platelet factor 4 complexes", Blood, Nov. 1, 2004, pp. 2791-2793, vol. 104, No. 9; prepublished Jun. 10, 2004.

Hayes et al. (2003) "Polymorphism in IgG Fc receptor FcgammaRIIIA gene in allogeneic bone marrow transplant recipients", Blood, (Nov. 16, 2003), vol. 102, No. 11, pp. 395b.

Kastbom et al. (2007) "Fcγ Receptor Type IIIA Genotype and Response to Tumor Necrosis Factor α-Blocking Agents in Patients With Rheumatoid Arthritis", Arthritis and Rheumatism, vol. 56(2) (Feb. 2007):448-452.

Kim et al. (2006) "FCGR3A gene polymorphisms may correlate with response to frontline R-CHOP therapy for diffuse large B-cell lymphoma", Blood, 108:2720-2725.

Louis et al., (2004) "Association between polymorphism in IgG Fc receptor IIIa coding gene and biological response to infliximab in Crohn's disease," Alimentary Pharmacology & Therapeutics, 19(5): 511-519.

Marshall, A. et al. (1997) "Getting the right drug into the right patient", Nature Biotechnology, vol. 15, pp. 1249-1252.

Miescher et al. (2004) "A single recombinant anti-RhD IgG prevents RhD immunization: association of RhD positive red blood cell clearance rate with polymorphisms in the FCγRIIA and FCγRIIIA genes," Blood 103(11): 4028-4035.

Mitrovic et al. (2007) "FCγRIIIA and FCγRIIA polymorphisms are not associated with response to rituximab and CHOP in patients with diffuse large B-cell lymphoma", Haematologica 92: 998-999.

Musolino et al. (2008) "Immunoglobulin G Fragment C Receptor Polymorphisms and Clinical Efficacy of Trastuzumab-Based Therapy in Patients With HER-2/*neu*-Positive Metastatic Breast Cancer", J. Clin. Oncol. vol. 26. No. 11 (Apr. 10, 2008), 1789-1796.

Opposition against European Patent No. 1 436 427 B1 (European Application No. 02 78 2887.0) May 5, 2009.

Pennell et al. (2008) "Lack of prognostic value of *FCGR3A-V158F* polymorphism in non-Hodgkin's lymphoma", Haematologica, 93:1265-1267.

Pouplard et al. (2003) "The Homozygous FCGR3A-158V Genotype: A Risk Factor for Heparin-Induced Thrombocytopenia in Patients with High Levels of Antibodies to Platelet-Factor 4?", vol. 102 (11):535a-536a, (Nov. 16, 2003) abstract for the 45th Annual Meeting of the American Society of Hematology held in San Diego, CA, USA on Dec. 6-9, 2003.

Scallon et al. (1995) "Chimeric Anti-TNF-α Monoclonal Antibody cA2 Binds Recombinant Transmembrane TNF-α and Activates Immune Effector Functions", Cytokine vol. 7. No. 3 (Apr. 1995): pp. 251-259.

Takagi et al. (1997) "Prediction of effect of interferon on chronic hepatitis C," Digestive Diseases and Sciences 42(11):2270-2276.

Treon et al. (2005) "Polymorphisms in FcγRIIIA (CD16) Receptor Expression Are Associated With Clinical Response to Rituximab in Waldenstrom's Macroglobulincmia", J. Clin. Oncol. vol. 23. No. 3 (Jan. 20, 2005), 474-481.

Tutuncu et al. (2005) "Fcγ Receptor Type IIIA Polymorphisms Influence Treatment Outcomes in Patients With Inflammatory Arthritis Treated With Tumor Necrosis Factor α-Blocking Agents", Arthritis and Rheumatism, vol. 52(9) (Sep. 2005):2693-2696.

Ulfgren et al. (2000) "Systemic Anti-Tumor Necrosis Factor α Therapy in Rheumatoid Arthritis Down-Regulates Synovial Tumor Necrosis Factor α Synthesis". Arthritis & Rheumatism vol. 43, No. 11, (Nov. 2000),pp. 2391-2396.

Cartron et al. "Therapeutic activity of humanized anti-CD20 monoclonal antibody and polymorphism in IgG Fc receptor FcγRIIIa gene", 43rd Annual Meeting of the American Society of Hematology *Blood*, Nov. 16, 2001, 98(11): p. 602a.

* cited by examiner

FcγRIIIa protein sequence (GenBank RefSeq NP_000560), 158-F allotype

```
                              10         20         30         40         50         60         70         80         90        100
protein                        1         10         20         30         40         50         60         70         80         90        100
mature protein                                                  1         10         20         30         40         50         60         70
NP_000560 (FcγRIIIa)  MWQLLLPTALLLLVSAGMRTEDLPKAVVFLEPQWYRVLEKDSVTLKCQGAYSPEDNSTQWFHNES  LISSQASSYFIDAATVDDSGEYRCQTNLSTLSDPV 110        120        130        140        150        160        170        180        190        200
protein                      101        110        120        130        140        150        160        170        180        190        200
mature protein                80         90        100        110        120        130        140        150        160        170        180
NP_000560 (FcγRIIIa)  QLEVHIGWLLLQAPRWVFKEEDPIHLRCHSWKNTALHKVTYLQNGKGRKYFHHN  SDFYIPKATLKDSGSYFCRGLFGSKNVSSETVNITITQGLAVSTIS 210        220        230        240        250
protein                      201        210        220        230        240        250
mature protein               190        200        210        220        230
NP_000560 (FcγRIIIa)  SFFPPGYQVSFCLVMVLLFAVDTGLYFSVKTNIRS  STRDWKDHKFKWRKDPQDK
```

FIGURE 3

*FCGR3A* gene (GenBank AL590385, complementary strand), 4985-T allele, coding for the 158-F allotype
Alignments with cDNA (GenBank RefSeq NM_000569) and protein (GenBank NP_000560)

Fig. 4A

Fig. 4B

```
-3200  gaacagcttccctgctctccaagacctttcagtccacaaatgcaatgagtttacagagagagaagcacaagctcctaaaggagttgggtgggttgggg
-3100  tcagaacctaatttagaaaattgaggaagtctcaactgcattacaatgcagttaatcagcagttggtgttaccaaatatgaaccaacaattt
-3000  tatctgcattatctcatttaagccatgagtgccagacccagttattgttagcctcacttggaacctgtgcttctccttgtagtactcactgtgaactacatcca
-2900  gggatttcctccagattcctgtgagacccagactctgcaaaatgacagtctcaagtctttgctcatgctgctcctcttgcctgaatgcctatttct
-2800  actacactgtgtgaactacagcagctctgaatatttgcgatctaatttaaagtgttctctccatgtacactcaagtgtctcctcagataaactagaaaactgtagtctagaggatgac
-2700  ctcaaaatcttcctgcttctgcagcatttcataatactgtcagtcgtcctagcactgtcacgtgcctgctccgccttcccctaaaactatgttcccctaagaaactgtaagtctagaggatgac
-2600  gcataacagcatttcataatactgtcacgtgcctgctccgccttcccctaagaaactgtaagtctagaggatgac
-2500  aatcaactgacaaacatgtgaagataaacactcaatatatgatatccaagacatctacactttttaaaaatttgctttttttccccccaagagt
-2400  aagaaaagcaaacatgagtaaaacactcaagactcaatactttgttttttttcccccccaagagt
-2300  caggtctcactctgtgccagctagagtgcatgacgtgcatgaacaatcctctgcctaggctgt
-2200  cctggtagctgggactacaggcgcatgcaaccaccatctgctattatatatattagtagagatggggtttcttctattggcctaggctgt
-2100  ctccaaattcctgctcactcccaagcatttccacctcacaattgcctccaaagtgctgggattacaaccactgagccaaatcccctgaaacttccatcctgtt
-2000  cattactgtaaaattaaccttagaaatccaaactcaatttgagaatttgcagctcagaagtgaaggcttgttctgcttaggctcagagcagacc
-1900  gcagtccctttctctcctcctgtgctctctcatctagccacccatttctctatctagccacttgcagctcagaagtgaaggcttgttctgcttaggctcagagcagacc
-1800  aaaggagtcaaataagaaatcaagacctcaaagaagaaaacaaagtgaaggccttagccctgaaggcttgttctgcttaggtttccagataagcatccgaa
-1700  aagaggagtcaaataagaaatcaagacctcaaagaagaaaacaaagtgaaggccttagccctgaaggcttgttctgcttaggtttccagataagcatccgaa
-1600  gtgctacagcaaggaactttaagttccagatactgtctgatttgcaagactctgtgtgtggcgggggaggtttaggtcattctgagtagaagagcattcattt
-1500  catttccattgtccaatccaaccaggcacctgtcagcctgtgcaaatgaaacacacccctaacaagtatcagtgccactatcaagcagagtcatctgatttttctgcctctggcttt
-1400  ataqcaaaqttggcggcacctgtcagcctgtgcaaatgaaacacacccctaacaagtatcagtgccactatcaagcagagtcatctgatttttctgcctctggcttt
-1300  ttctgagcagttgaggccacctgtccagatcgagagaatcctgacgacgtacgggggagaattctgagagagaaaactgcccacccccaccttctgccaccccccaccttctgcaccctttct
-1200  ttgtgagtaacaactgtgagcccccgtcctgtccggcttccctcgcccgtccttacgttccgcccttcgctggccttccttcgcccgtccttacgttccgcccttcgctggccttccttcgcccgtcc
-1100  gqtaaqqaqcccctqqqtaaaaqaqttcctqtctqtttcttctaacctqqaaatctaatqatcaaatcacactaaaaaqtcaqtcctqtqattacatatccaqqaqcatataqa
-1000  aggaaggtaaagagttcctgtctgtttcttctaacctggaaatctaatgatcaaatcacactaaaaagtcagtcctgtgattacatatccaggagcatataga
-900  tctaccctacctgggtttcttgaatttgaaagaaattctgctgtgagataatattgaggcagagaacactgctgagtgtctgaagatttgaaaggacacttctgtgtg
-800  tttgaatttgaatttgaaagaaattctgctgtgagataatattgaggcagagaacactgctgagtgtctgaagatttgaaaggacacttctgtgtg
-700  cagcagggctgcagctgagatagatggttctgggcaggagatgggcaggagaccaacactttctgaggtgaaatgaaggaagccctcagagaatgctcctccca
-600  ccttgaatctcatcccaggtctcactgtcctgtctgcagatgctcagcagcagactgctcagactctcagacttgcctcagctctttccttc
-500  ctctgcagattctgtgtgtggggctgtttctatgggtgtgtcctgatgctgctgcagcctgcagactcagatgaaagtttcaagaaaggaaatggttgacagagatggtgg
-400  ctgtcctgttctatggtggggctgtttctatggtgtgtgtcctgatgctgctgcagcctgcagactcagatgaaagtttcaagaaaggaaatggttgacagagatggtgg
-300  agggctggggaaaggctgttacttcctcctcctgtcctcagtcgtttctagtcgtttggtccctttaggtcggttgtccctttaggctccggatatctttggtgacttgtccactgtccagtgcatc
-200  agggctggggaaaggctgttacttcctcctcctgtcctcagtcgtttctagtcgtttggtccctttaggtcggttgtccctttaggctccggatatctttggtgacttgtccactgtccagtgcatc AL590385   -100               -90               -80               -70               -60               -50               -40               -30               -20               -10                -1
NM_000569  agggctggggaaaggctgttacttcctcctgtcctcagtcgtttctagtcgtttggtccctttaggctccggatatctttggtgacttgtccactgtccagtgcatc
                                                                                                tctttggtgacttgtccactgtccagtgcatc
                                                                               exon 1 (5'-UTR)
```

Fig. 4C

```
n°          1          10         20         30         40         50         60         70         80         90         100
AL590385    atgtgcagctgctcctcccaactgctctgctacttctaggtaagtcaggttctccctgttgagggagaagtttgagatgccttgggttcagcagagac
NM_000569   atgtgcagctgctcctcccaactgctctgctactttctag
NP_000560    M  W  Q  L  L  L  P  T  A  L  L  L  L
                                         exon 1

AL590385  101  ccctttcaggctacgagctgaatgagactcccacgaaggatggaaccctcaccacatctatagctgtgtgattagctctaggacaagccaagatgggcta
AL590385  201  gaaatgaggagaatgctgttccaattgggcatactcatgggtgaggcagtcactcaccctctgggtcccagaatcactctgtgaaccaaagagc
AL590385  301  ttcgactagatggtcctaggtctgtctctttcagttgacattccaggttctcctcatgattttcaattcttcacccttcttcttgtgggatatggt
AL590385  401  tgaggctctttctgtagctgttcaggagaattcaacctgtaccctaatttgagtttgcacagggagcaaggggagcagtgttgaaaata
AL590385  501  gggattttgttgacagtggcacagtggcgcaagagcatgacagtgacagagacaggttctccaccagaaacatctgattcttgggaaaattg
AL590385  601  ggctcctgggcagagaggaggcaggggagtttaaactactctatgtttcaataactactaatcactctgatctctgccctactcaatatttgattatctttttct AL590385  701  tgcagtttcagctggactgcgatcatgcgacttggagtcagcttcatggtcttgattgaccagtggggcacatatgggacaaaggccataagatattgggaaa                                                800
NM_000569      tttcagctgcatgcggactg
NP_000560       V  S  A  G  M  R  T
                             exon 2

AL590385  801  tgctttgttgaatggaaaatgctgatgtggggttagcaggatagttcctccaacacagcagaacttgccctgtgctctctgccagctttccttaag
AL590385  901  atactgaacaggccaaaaatgccaagatgctctaagactgggtttgcaatgagtcattctgctttgaggctccctgggaat 1010       1020       1030       1040       1050       1060       1070       1080       1090       1100
NM_000569     ggcagtgtagagcctgctctccctgtcctcaccccattatcttggctcctcagaagatctccagaaggctgtgttcctggagcctcaatggt
NP_000560                                                                                E  D  L  P  K  A  V  V  F  L  E  P  Q  W
                                                                                                                exon 3

1110       1120       1130       1140       1150       1160       1170       1180       1190       1200
NM_000569     aagatctcccaaaggctgtgttcctggagcctcaatggtacagggtgctcgagaaggacagtgtgactctgaaagtgccaggagcctactcccctgagacaattccacacagtggtttcacacagtgagacctcatctc
NP_000560                                                                           E  D  L  P  K  A  V  V  F  L  E  P  Q  W 1210       1220       1230       1240       1250       1260       1270       1280       1290       1300
NM_000569     aagccaggcctgagctacttcattgacgctgccacagtgccacagtgccgacgacagtggagagtacaggtggagagtacaggtgccagacaaacctctccaccctcagtgaccgtgcag
NP_000560      Y  R  V  L  E  K  D  S  V  T  L  K  C  Q  G  A  Y  S  P  E  D  N  S  T  Q  W  F  H  N  E  S  L  I  S
                                                                    exon 3

1210       1220       1230       1240       1250       1260       1270       1280       1290       1300
AL590385      aagccaggcctgagctacttcattgacgctgccacagtgccacagtgccgacgacagtggagagtacaggtggagagtacaggtgccagacaaacctctccaccctcagtgaccgtgcag
NM_000569     aagccaggcctgagctacttcattgacgctgccacagtgccacagtgccgacgacagtggagagtacaggtggagagtacaggtgccagacaaacctctccaccctcagtgaccgtgcag
NP_000560      S  Q  A  S  S  Y  F  I  D  A  A  T  V  D  D  G  E  Y  R  C  Q  T  N  L  S  T  L  S  D  P  V  Q
```

```
AL590385  6301  ctctgtcaaacaagcaggagcctttgctgctcagtgttgtggctgtgctgtcctgctcagatagcactaagatcaggaaccaatggaggaagcaatactttc
AL590385  6401  cccagacttcccaccattcctaccacttgcctgttgctgttgctgttgtcaaagactttctactggtgacctactgtttgttccaaatatctgcctagtga AL590385  6501       6510      6520      6530      6540      6550      6560      6570      6580      6590      6600
          6501  ctgtcattttttcatctctcccacttcctctaataggttggcagtgtcaaccatctcatcattcttccacctgggtaccaagtctcttttctgcttgg
NM_000569                                            gtttgcagtgtcaaccatctcatcattcttccacctgggtaccaagtctcttttctgcttgg
NP_000560                                              G  L  A  V  S  T  I  S  S  F  F  P  P  G  Y  Q  V  S  F  C  L
                                                                                                          exon 5

AL590385  6601       6610      6620      6630      6640      6650      6660      6670      6680      6690      6700
          6601  tgatggtactccttttgcagtggacacaggactatattctctgtgaagacaaacattgaagctcaacaagagactgaaggaccataaatttaaatg
NM_000569       tgatggtactccttttgcagtggacacaggactatattctctgtgaagacaaacattgaagctcaacaagagactgaaggaccataaatttaaatg
NP_000560        V  M  V  L  L  F  A  V  D  T  G  L  Y  F  S  V  K  T  N  I  R  S  S  T  R  D  W  K  D  H  K  F  K  W
                                                                                      exon 5

AL590385  6701       6710      6720      6730      6740      6750      6760      6770      6780      6790      6800
          6701  gagaaggacctcaagacaaatgaccccatccatgggggtaataagagcagtagcagcagcatctctgaacattctctgattgcaaccccatca
NM_000569       gagaaggacctcaagacaaatgaccccatccatgggggtaataagagcagtagcagcagcatctctgaacattctctgattgcaaccccatca
NP_000560        R  K  D  P  Q  D  K  -
                                     exon 5                                                   exon 5 (3' UTR)

AL590385  6801       6810      6820      6830      6840      6850      6860      6870      6880      6890      6900
          6801  tcctcaggcctctctacaagcagcaggaaacatagaactcagagaactgcagatcccctatccaacctctgacttttcctggtctccagtgaggaaggaaaagc
NM_000569       tcctcaggcctctc
                      exon 5 (3' UTR) ...

AL590385  6901  ccatgatcttcaagcaggaagcccagtagtagctgcattcctagaaattgaagtttcagctgcacaaacacttttctgtcccaaccgttccctc
          7001  acagcaaagcaacaatacaggctaggatgataatccttaaacatacaaaattgctcgtgttataaattaccagtttagagggaaaaaacaat
          7101  tattcctaaataaatggataagtagaattaatgttgaggaggaccatacagagtgtgggaactgctgggatcgtcagggaattcagtggaccaatgaa
          7201  agcatggctgagaaatagcaggtagcaggtagtccaggatagtcttaaggaggctcttccatctgagccccagagataaggtgtcttcctagaacattagccgtagt
          7301  ggaattaacaggaaatcatgaggtgactgaggtcttccaggggactcttcagagatgagtcttccaagtatataacgatgagtcctctta
          7401  atgctaggagtaagtgaacagaactatctcagctagaatgagaatggttaatgcaggactgaaaagaaccacacagaagaaagcgcaggaggtgaaa
          7501  agttgctaagtgacacaaatgtcctcagagaatgagaaagtttcaggactgtaaacccacctttctgcttcaatctaattcctgtgtttcat
          7601  atgctttcttggccaggtagtagaatttgtatactaaatactatctgagctgcgtagttaagttatgaaactttcaaatcctcatcatgtcagttc
          7701  tgcattattaaacaaatgttgataaatcttgcttatagataagaaagttttagctgtctgttttgtaagcttttgtaagcgcaacattcttgttccaata
          7801  caatgagtgtggcgggaagaacaattgtgctactctgaagatggttgaaaccatgtaataaaatatgataataataagcttcccttgtcc
          7901  aagcattttacagatcttgcatgctacttcttagatagaagaaaactaccccctcctcccaacaccccatccccaacactaaaattagccagcttgctttccaa
```

```
8101  atcttgctgagacaattgggctaaggagattcttatggaagtatggatagagggtgaataagcattagagatcgtttagagcattgggcagata
8201  ggagaaggcacagctacataatattacataagattccgacacgacacagtgcatttggaaacctttgtgatgtgatagcgcattcaactcacattgaaacctggaaacagctcatttactactaagacgattcaagcta
8301  gattgcatacatataatattacataagattccgacacgacacagtgcatttggaaacctttgaaaccttgaaacagtttattctagtgagaaaacagtaaataggaagagaa
8401  agcttgagttcaggtgctgaagatacccagatgaacaacacagattgggggtgtggtcatgaaggatgaagtaggagttccgccaggcaagagaggaagagaaagcccaagtt
8501  tgaagaaagggctgcagaaaagaggcttgatttgggggtgtggtcatgaaggatgaagtaggagttccgccaggcaagagagagaagagaaagcccaagtt
8601  cataggcaaagattccaaaactaaggagatcgtatcagaccctgcaatacattgagagagttaagcagaccaggttttgtaccgtatagtattttagaagattc
8701  gcattaccttccaactacttgatgatgcacggacaggaaggtgaagacagaagcaaataggaggcacaaataaggacacagtcagtaaccaagatagc
8801  tctccaactacttgatgatgcacggacaggaaggtgttaataacaagtatttaggaggccgactctccaagatgcacaagatgcagccagcagtacacggcgtga
8901  gaagtaactggtgcgcccacacatagtgccgtttctcagtaaatttcttaaagtgtcagttccataagtcatagtggtgttaagcacagctaagagtttgtgctaccagagct
9001  ctaaggaccaggttccacacatagtgccgtttctcagtaaatttcttaaagtgtcagttccataagtcagttgctaagcagttgcagctaagagtctcacgtctaagagaccgc
9101  tattattagtacttccttggtcagtaaatttcttaaagtgtcagttccataagtcagttgctaagcagctaagagtctcacgagct
9201  ccctagtcggaaaaaccaaataccctcaaattacccgtacagctacagtcagacaagctgaaccacacaacgcacagttttcagtcaagttcaaaaaccc
9301  ccctgcggttagcaccgcgctgttccgtccctggtggcgccaagccctcgagcgatagcatccaaaaaaaattgaggtatcgcgctaaccgatgcgcacaagacgggc
9401  aggttcacaaaatgcgacttccgtccctggtggcgccaagccctcgagcgatagcatccaaaaaaattgaggtatcgcgctaaccgatgcgcacaagacgggc
9501  gttggcgattttggctgccaagtcacttcactcagtccctgagcgaggcaggtcttttttctgcgctagcactgcctagatctggagcaggactcagcttccag
9601  agctttccgtgcttcagggcggctcatagccctgagcgaggcaggtcttttttctgcgctagcactgcctagatctggagcaggactcagcttccag
9701  cagagaggttgagagaagggagcagaagaatgcaagaacgaaggtcttcgggaatccaaaatgatgctccctgtggttcggggttccgttg
9801  atttttgtcagagaagtacgataagcttttcttcagtccaaatcacgtccgcgtatattagacatgtgatgtctaagtgagtttgtcgtgactcataataagctatt
9901  atcgtgagcattaaaaatattttcttcaccggcatattagacatgtgatgtctaagtgagtttgtgttacaaaatttgttaaaattagtcttcaacc
10001 cacgctgttgaaaggtttctaccggcatattagacatgtgatgtctaagtgagcttaaaaagctgtaacattccaattaatgtattcagcttga
10101 aataaaaatattttaaaaaaatgctgcaactcagtgctgtctggtctcaaaaagcttttttttcttaattcatatgtatatactttattcatagacacagagacctccattccaccac
10201 catcgacctaggagaaaccttcagtgctgtctggtctcaaaaagcttttttttcttaattcatatgtatatactttattcatagacctcatctgtcatctcattaggtgttt
10301 aagttctaggctacatgtgcacaaggtcaggtcgttacatatacacgacagtccgggtgtgatgttcctaccatgcacacgtatgtttattgtgaactattcaca
10401 ctccctaatgttatcctccctccttccccacaaatgtgaatcaatgatgactcgttaagaactgatcacagtggatacaatccacaagcagaaaatcagacagaatatcagcataaaaa
10501 ataagcaaagacttgaaccaaccaaatgtccatcaatgatgactcgttaagaactgatcacagtggatacaatccacaagcagaaaatcagacagaaatcagcataaaaa
10601 aggatggttcatgtcctttgtaggaacataagaacacttgaacatagaaccacttggacgaaagccatttctctatattgccaaaaccacaggtgtctccatagcctccacagaatctc
10701 actcatagtgggaattgaaccaataagaacacttggacgaaagccatttctctatattgccaaaaaccacaggtgtctccatagcctccacagaatctc
10801 ctttctttctgccctgccatcctcgtcatcagtggctccagtttaggagcaggtgaagttttcaatgatgtcagtgaagagacatgcaaac
10901 atagatgttaaactagagtcattattatcagaaattacagaaattacaaattttttttttgatgattggagtcttgcctctgccatgccatgccatgccaagccagtctgcgcaatcttg
11001 tgatcttaaactagagtcacctcacctccacctccctgtccgcccaggttgagtgcgcattgtgccaccatgccaccatgccacggctaattt
11101 gctcactgcaacctcacctccctttttttttgagacaggagtctcgctctgtcgcccaggttgagtgcgcattgtgccaccatgccaccatgccacggctaattt
11201 ttgtatttttttttttgtagagacggagtctcgctctgtcgcccaggttgagtgcgcattgtgccaccatgccaccatgccacggctaattt
11301 atccacgccattctcctgcctcagcctcccgagtagctggactacaggcacacgccaccatgccacggccaccatgccaccatgccacggctaattt
11401 tttctatgttgcaggatcattttttatacttttaaattttttgtctctttgtctctttctttctttctttctttctttttttttttttttttttttttttttttttttttttttt
11501 ccaggctagagtgcagtggctcattcagctcctgcagagcctcccgagtagctggactacaggcacacgccaccatgccaccatgccaccatgccacggctaattt
11601 actgccaggaagctccattgtcaccgacgagatcagaagctagttgcatggtaaatgcaaagaaaatatatatatatatatatatatatatatatatatatatatatatatatatatat
11701 gaggtgcttctcatgcaagggaattggctggaaaaaataggagagggtgcaatgagcaaatagcccagctgagaagtgtgcaggcaacagcaagaaaatc
11801 catccagcatagactagatgtgtgcacactgcacagcagcagcagcagcagcagcagcagcagcagcagcagcagcagcagcagcagcagcagcagcagcagcagcagcagcag
11901 acagcctttgtacctgatgattgcttaatttattgaaaaaaatgaagtcctgtatcaggggaaccagccaccatttcattgaggtct Fig. 4H
```

METHODS AND COMPOSITIONS TO EVALUATE ANTIBODY TREATMENT RESPONSE

This application is the U.S. national stage application of International Patent Application No. PCT/EP02/011397, filed Oct. 11, 2002, which claims the benefit of application EP 01402718.9, filed Oct. 19, 2001.

The present invention relates to methods and compositions to evaluate or assess the response of a subject to particular therapeutic treatment. More particularly, the invention provides methods to determine the response of subjects, or to adapt the treatment protocol of subjects treated with therapeutic antibodies. The invention can be used for patients with malignancies, particularly lymphoma, and is suited to select best responders and/or adjust treatment condition or protocol for low responders.

INTRODUCTION

Various therapeutic strategies in human beings are based on the use of therapeutic antibodies. This includes, for instance, the use of therapeutic antibodies developed to deplete target cells, particularly diseased cells such as virally-infected cells, tumor cells or other pathogenic cells, including allogenic immunocompetent cells. Such antibodies are typically monoclonal antibodies, of IgG species, typically IgG1 and IgG3. These antibodies can be recombinant antibodies and humanized antibodies, comprising functional domains from various species or origin or specificity. A particular example of such therapeutic antibodies is rituximab (Mabthera®, Rituxan®), which is a chimeric anti-CD20 IgG1 monoclonal antibody made with human γ1 and κ constant regions linked to murine variable domains[1]. For a few years, rituximab has been considerably modifying the therapeutical strategy against B lymphoproliferative malignancies, particularly non-Hodgkin's lymphomas (NHL). Other examples of intact humanized IgG1 antibodies include alemtuzumab (Campath-1H®), which is used in the treatment of B cell malignancies or trastuzumab (Herceptin®), which is used in the treatment of breast cancer. Additional examples of therapeutic antibodies under development are disclosed in the art.

While these antibodies represent a novel efficient approach to human therapy, particularly for treatment of tumors, they do not always exhibit a strong efficacy and their use could be improved by evaluating the response of subjects thereto. For instance, while rituximab, alone or in combination with chemotherapy was shown to be effective in the treatment of both low-intermediate[2-8] and high-grade NHL[6,9], 30% to 50% of patients with low grade NHL have no clinical response to rituximab[4,5]. It has been suggested that the level of CD20 expression on lymphoma cells[2], the presence of high tumor burden at the time of treatment[6] or low serum rituximab concentrations[2] may explain the lack of efficacy of rituximab in some patients. Nevertheless, the actual causes of treatment failure remain largely unknown.

The availability of methods allowing the evaluation of patient response to antibody treatment would greatly enhance the therapeutic efficacy of these products. However, the precise mode of action in vivo of such therapeutic antibodies is not clearly documented. Indeed, while in vitro studies suggest various possible modes of action of rituximab (antibody-dependant cell-mediated cytotoxicity (ADCC)[10,11], complement-dependant cytotoxicity[10,12,13], direct signalling leading to apoptosis[14,15], etc.), the clear action of these target cell-depleting antibodies in vivo is not documented in humans. Furthermore, while ADCC is an important effector mechanism in the eradication of intracellular pathogens and tumor cells, the role of an ADCC is still controversial[12,13].

The present invention now proposes novel methods and compositions to assess the therapeutic response of a subject to a therapeutic antibody. The invention also proposes methods to select patients having best responding profile to therapeutic antibody treatment. The invention also relates to methods of treating patients with therapeutic antibodies, comprising a prior step of evaluating the patient's response. The invention also relates to compositions and kits suitable to perform the invention. The invention may as well be used in clinical trials or experimental settings, to assess or monitor a subject's response, or to verify the mode of action of an antibody.

The invention is based, in part, on the demonstration of a correlation between the genotype of a subject and its ability to respond to therapeutic antibody treatment. More specifically, the invention shows that the genotype of the FcγRIIIa receptor directly correlates with the subject's response to therapeutic antibody treatment.

Three classes of FcγR (FcγRI, FcγRII and FcγRIII) and their subclasses are encoded by eight genes in humans, all located on the long arm of chromosome 1. Some of these genes display a functional allelic polymorphism generating allotypes with different receptor properties. These polymorphisms have been identified as genetic factors increasing the susceptibility to autoimmune or infectious diseases[19-21]. One of these genetic factors is a gene dimorphism in FCGR3A, which encodes FcγRIIIa with either a phenylalanine (F) or a valine (V) at amine acid position 158[22,23]. This residue directly interacts with the lower hinge region of IgG1 as recently shown by IgG1-FcγRIII co-cristallization[24]. It has been clearly demonstrated that human IgG1 binds more strongly to homozygous FcγRIIIa-158V natural killer cells (NK) than to homozygous FcγRIIIa-158F or heterozygous NK cells[22,23].

We undertook to evaluate a possible correlation between the FCGR3A genotype and a patient response to therapeutic antibody treatment in vivo. Our invention stems in part from the unexpected discovery that a very strong correlation exists between said genotype and said response profile, the presence of a valine residue at position 158 being indicative of a high response rate. More specifically, the genotyping of FCGR3A was performed in patients with previously untreated follicular NHL who had received rituximab alone, a particular situation in which the response rate is very high[5]. The FCGR2A-131H/R was also determined as control since this gene co-localizes with FCGR3A on chromosome 1q22 and encodes the macrophage FcγRIIa receptor.

The FCGR3A-158Y/F genotype was determined in 47 patients having received rituximab for a previously untreated follicular non-Hodgkin's lymphoma. Clinical and molecular response were evaluated at two months (M2) and at one year (M12). Positive molecular response was defined as a disappearance of the BCL2-JH gene rearrangement in both peripheral blood and bone marrow. FCGR3A-158V homozygous patients were 21% whereas FCGR3A-158F homozygous and heterozygous patients (FCGR3A-158F carriers) were 34% and 45%, respectively. The objective response rates at M2 and M12 were 100% and 90% in FCGR3A-158V homozygous patients compared with 65% (p=0.02) and 51% (p=0.03) in FCGR3A-158F carriers. A positive molecular response was observed at M12 in 5/6 of homozygous FCGR3A-158V patients compared with 5/16 of FCGR3A-158F carriers (p=0.04). Furthermore, the homozygous FCGR3A-158V genotype was confirmed to be the single parameters associated with clinical and molecular responses in multivariate analysis and was also associated with a lower rate of disease progression (p=0.05).

Accordingly, the present invention establishes, for the first time, an association between the FCGR3A genotype and clinical and molecular responses to therapeutic antibodies. The invention thus provides a first unique marker that can be used to monitor, evaluate or select a patient's response. This invention thus introduces new pharmacogenetical approaches in the management of patients with malignancies, viral infections or other diseases related to the presence of pathological cells in a subject, particularly non-Hodgkin's lymphoma.

An object of this invention resides in a method of assessing the response of a subject to a therapeutic antibody treatment, comprising determining in vitro the FCGR3A genotype and/or the presence of a polymorphism in the FcγRIIIa receptor of said subject. More specifically, the method comprises determining in vitro the FCGR3A158 genotype of said subject.

A further object of this invention is a method of selecting patients for therapeutic antibody treatment, the method comprising determining in vitro the FCGR3A genotype and/or the presence of a polymorphism in the FcγRIIIa receptor of said subject. More specifically, the method comprises determining in vitro the FCGR3A 158 genotype of said subject.

An other object of this invention is a method of improving the efficacy or treatment condition or protocol of a therapeutic antibody treatment in a subject, comprising determining in vitro the FCGR3A genotype and/or the presence of a polymorphism in the FcγRIIIa receptor of said subject. More specifically, the method comprises determining in vitro the FCGR3A 158 genotype of said subject.

More specifically, determining in vitro the FCGR3A158 genotype of a subject comprises determining amino acid residue at position 158 of FcγRIIIa receptor (or corresponding codon in the FCGR3A gene), a valine at position 158 being indicative of a better response to said treatment and a phenylalanine at position 158 being indicative of a lower response to said treatment.

Within the context of this invention, the term "therapeutic antibody or antibodies" designates more specifically any antibody that functions to deplete target cells in a patient. Specific examples of such target cells include tumor cells, virus-infected cells, allogenic cells, pathological immunocompetent cells (e.g., B lymphocytes, T lymphocytes, antigen-presenting cells, etc.) involved in allergies, autoimmune diseases, allogenic reactions, etc., or even healthy cells (e.g., endothelial cells in an anti-angiogenic therapeutic strategy). Most preferred target cells within the context of this invention are tumor cells and virus-infected cells. The therapeutic antibodies may, for instance, mediate a cytotoxic effect or a cell lysis, particularly by antibody-dependant cell-mediated cytotoxicity (ADCC). ADCC requires leukocyte receptors for the Fc portion of IgG (FcγR) whose function is to link the IgG-sensitized antigens to FcγR-bearing cytotoxic cells and to trigger the cell activation machinery. While this mechanism of action has not been evidenced in vivo in humans, it may account for the efficacy of such target cell-depleting therapeutic antibodies. The therapeutic antibodies may by polyclonal or, preferably, monoclonal. They may be produced by hybridomas or by recombinant cells engineered to express the desired variable and constant domains. The antibodies may by single chain antibodies or other antibody derivatives retaining the antigen specificity and the lower hinge region or a variant thereof. These may be polyfunctional antibodies, recombinant antibodies, ScFv, humanized antibodies, or variants thereof. Therapeutic antibodies are specific for surface antigens, e.g., membrane antigens. Most preferred therapeutic antibodies are specific for tumor antigens (e.g., molecules specifically expressed by tumor cells), such as CD20, CD52, ErbB2 (or HER2/Neu), CD33, CD22, CD25, MUC-1, CEA, KDR, αVβ3, etc., particularly lymphoma antigens (e.g., CD20). The therapeutic antibodies are preferably IgG1 or IgG3, more preferably IgG1.

Typical examples of therapeutic antibodies of this invention are rituximab, alemtuzumab and trastuzumab. Such antibodies may be used according to clinical protocols that have been authorized for use in human subjects. Additional specific examples of therapeutic antibodies include, for instance, epratuzumab, basiliximab, daclizumab, cetuximab, labetuzumab, sevirumab, tuvurimab, palivizumab, infliximab, omalizumab, efalizumab, natalizumab, clenoliximab, etc., as listed in the following table:

| Ab specificity | DCI | Commercial name | Typical Indications |
| --- | --- | --- | --- |
| Anti-CD20 | rituximab | MabThera ®, Rituxan ® | LNH B |
| Anti-CD52 | alemtuzumab | CAMPATH-1H ® | LLC, allograft |
| Anti-CD33 | | Zamyl ™ | Acute myeloid Leukemia |
| Anti-HLA-DR | | Remitogen ™ | LNH B |
| Anti-CD22 | epratuzumab | LymphoCide ™ | LNH B |
| Anti-erbB2 (HER-2/neu) | trastuzumab | Herceptin ®, | Metastatic breast cancer |
| Anti-EGFR (HER-1, erbB1) | cetuximab | | ORL and colorectal Cancers |
| Anti-MUC-1 | | Therex ® | Breast and epithelial cancers |
| Anti-CEA | labetuzumab | CEA-Cide ™ | |
| Anti-αVβ3 | | Vitaxin | Cancers (anti-angiogenic) |
| Anti-KDR (VEGFR2) | | | Cancers (anti-angiogenic) |
| anti-VRS fusion protein | palivizumab | Synagis ® | Viral diseases |
| Idem | | Numax ™ | Idem |
| CMV | sevirumab | Protovir | CMV Infection |
| HBs | tuvirumab | Ostavir ™ | Hepatitis B |
| Anti-CD25 | basiliximab | Simulect ® | Prevention/treatment allograft rejection |
| Anti-CD25 | daclizumab | Zenapax ® | Prevention/treatment allograft rejection |
| anti-TNF-α | infliximab | Remicade ™ | Crohn disease, polyarthrite rhumatoid |
| anti-IgE | omalizumab | Xolair ™ | Asthma |
| anti-integrin αL (CD11a, LFA-1) | efalizumab | Xanelim ™ | psoriasis |
| anti-CD4 | keliximab | | |
| anti-CD2 | siplizumab | | |
| Anti-CD64 | | | anemia |
| anti-CD147 | | | GvH |
| anti-integrin α4(α4β1-α4β7) | natalizumab | Antegren ® | Sclerosis, Crohn |
| Anti-integrin β7 | | | Crohn, RCH |
| anti-CD4* | clenoliximab | | |

Within the context of the present invention, a subject or patient includes any mammalian subject or patient, more preferably a human subject or patient.

Figure 4E:
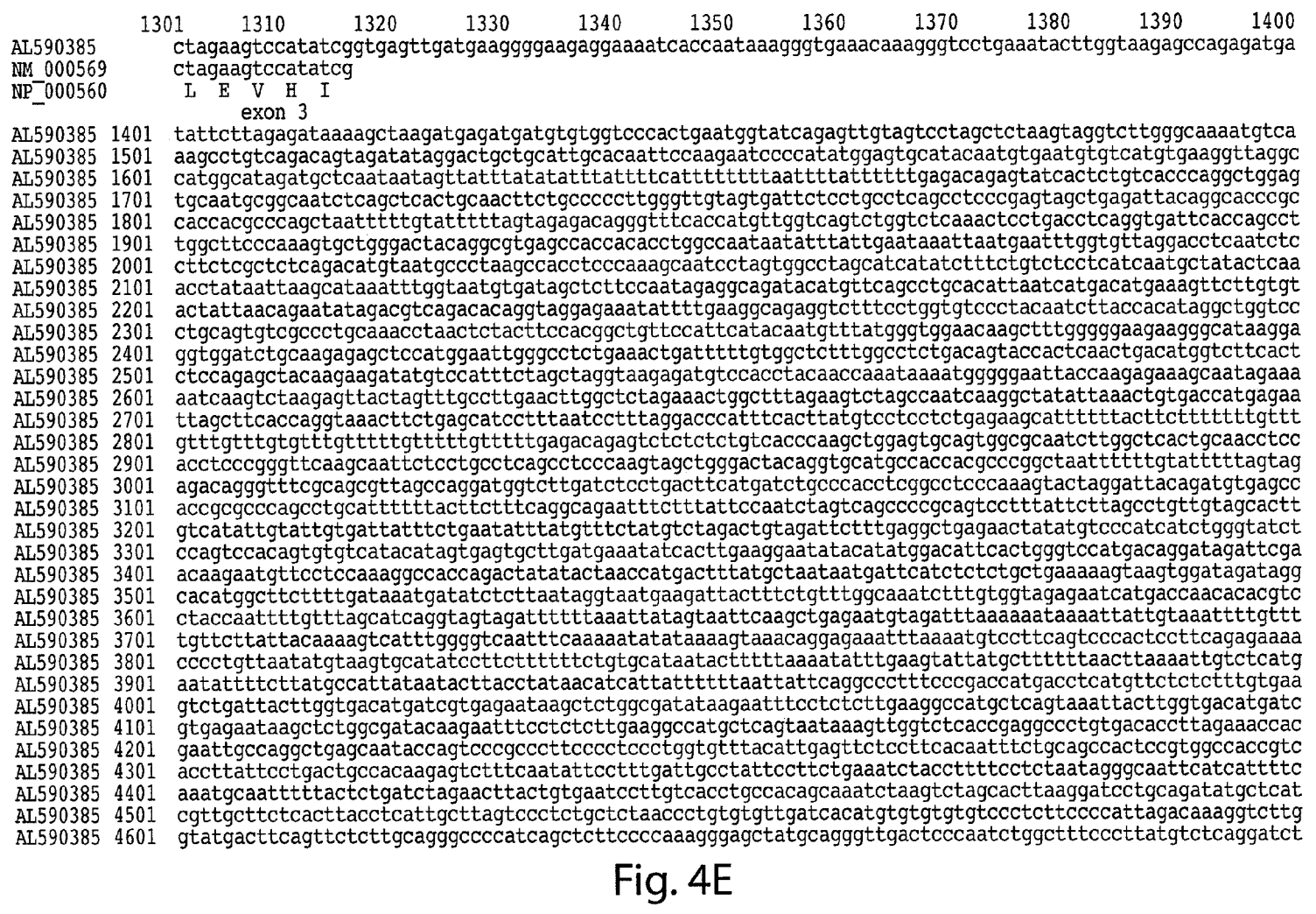
Figure 4F:
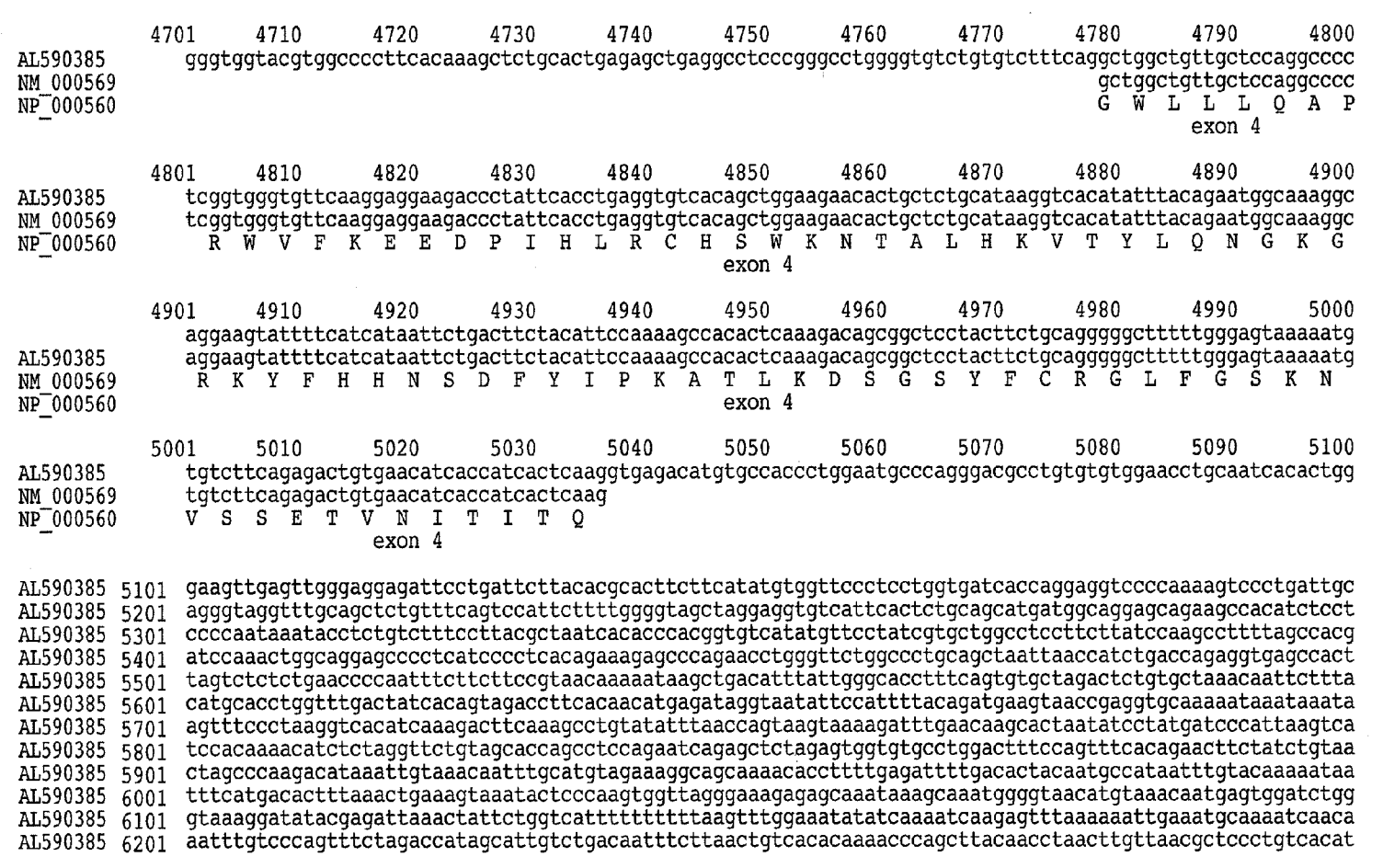

According to the invention the term FCGR3A gene refers to any nucleic acid molecule encoding a FcγRIIIa polypeptide in a subject. This term includes, in particular, genomic DNA, cDNA, RNA (pre-rRNA, messenger RNA, etc.), etc. or any synthetic nucleic acid comprising all or part of the sequence thereof. Synthetic nucleic acid includes cDNA, prepared from RNAs, and containing at least a portion of a sequence of the FCGR3A genomic DNA as for example one or more introns or a portion containing one or more mutations. Most preferably, the term FCGR3A gene refers to genomic DNA, cDNA or mRNA, typically genomic DNA or mRNA. The FCGR3A gene is preferably a human FCGRIIIa gene or nucleic acid, i.e., comprises the sequence of a nucleic acid encoding all or part of a FcγRIIIa polypeptide having the sequence of human FcγRIIIa polypeptide. Such nucleic acids can be isolated or prepared according to known techniques. For instance, they may be isolated from gene libraries or banks, by hybridization techniques. They can also be genetically or chemically synthesized. The genetic organization of a human FCGRIIIa gene is depicted on FIG. 2. The amino acid sequence of human FcγRIIIa is represented FIG. 3. Amino acid position 158 is numbered from residue 1 of the mature protein. It corresponds to residue 176 of the pre-protein having a signal peptide. The sequence of a wild type FCGR3A gene is represented on FIG. 4 (see also Genbank accession Number AL590385 or NM_000569 for partial sequence).

Within the context of this invention, a portion or part means at least 3 nucleotides (e.g., a codon), preferably at least 9 nucleotides, even more preferably at least 15 nucleotides, and can contain as much as 1000 nucleotides. Such a portion can be obtained by any technique well known in the art, e.g., enzymatic and/or chemical cleavage, chemical synthesis or a combination thereof. The sequence of a portion of a FCGR3A gene encoding amino acid position 158 is represented below, for sake of clarity:

chain reaction (PCR), such as simple PCR, RT-PCR or nested PCR, for instance, using conventional methods and primers.

In this regard, amplification primers for use in this invention more preferably contain less than about 50 nucleotides even more preferably less than 30 nucleotides, typically less than about 25 or 20 nucleotides. Also, preferred primers usually contain at least 5, preferably at least 8 nucleotides, to ensure specificity. The sequence of the primer can be prepared based on the sequence of the FCGR3A gene, to allow full complementarity therewith, preferably. The probe may be labelled using any known techniques such as radioactivity, fluorescence, enzymatic, chemical, etc. This labeling can use for example Phosphor 32, biotin (16-dUTP), digoxygenin (11-dUTP). It should be understood that the present invention shall not be bound or limited by particular detection or labelling techniques. The primers may further comprise restriction sites to introduce allele-specific restriction sites in the amplified nucleic acids, as disclosed below.

Specific examples of such amplification primers are, for instance, SEQ ID NO: 1-4.

It should be understood that other primers can be designed by the skilled artisan, such as any fragment of the FCGR3A gene, for use in the amplification step and especially a pair of primers comprising a forward sequence and a reverse sequence wherein said primers of said pair hybridize with a region of a FCGR3A gene and allow amplification of at least a portion of the FCGR3A gene containing codon 158. In a preferred embodiment, each pair of primers comprises at least one primer that is complementary, and overlaps with codon 158, and allows to discriminate between 158V (gtt) and 158F (ttt). The amplification conditions may also be adjusted by the

```
cDNA              540       550       560       570       580
genomic DNA          4970      4980      4990      5000.

158F allele    tcctacttctgcaggggggctttttgggagtaaaaatgtgtcttca
                S   Y   F   C   R   G   L   F   G   S   K   N   V   S   S
(SEQ
ID NO:
9)

158V allele    tcctacttctgcaggggggcttgttgggagtaaaaatgtgtcttca
                S   Y   F   C   R   G   L   V   G   S   K   N   V   S   S
(SEQ ID NO:
10)
```

As indicated above, the invention comprises a method of determining in vitro the FCGR3A158 genotype of said subject. This more particularly comprises determining the nature of amino acid residue present (or encoded) at position 158 of the FcγRIIIa polypeptide.

Genotyping the FCGR3A gene or corresponding polypeptide in said subject may be achieved by various techniques, comprising analysing the coding nucleic acid molecules or the encoded polypeptide. Analysis may comprise sequencing, migration, electrophoresis, immuno-techniques, amplifications, specific digestions or hybridisations, etc.

In a particular embodiment, determining amino acid residue at position 158 of FcγRIIIa receptor comprises a step of sequencing the FCGR3A receptor gene or RNA or a portion thereof comprising the nucleotides encoding amino acid residue 158.

In an other particular embodiment, determining amino acid residue at position 158 of FcγRIIIa receptor comprises a step of amplifying the FCGR3A receptor gene or RNA or a portion thereof comprising the nucleotides encoding amino acid residue 158. Amplification may be performed by polymerase skilled person, based on common general knowledge and the guidance contained in the specification.

In a particular embodiment, the method of the present invention thus comprises a PCR amplification of a portion of the FCGR3a mRNA or gDNA with specific oligonucleotide primers, in the cell or in the biological sample, said portion comprising codon 158, and a direct or indirect analysis of PCR products, e.g., by electrophoresis, particularly Denaturing Gel Gradient Electrophoresis (DGGE).

In an other particular embodiment, determining amino acid residue at position 158 of FcγRIIIa receptor comprises a step of allele-specific restriction enzyme digestion. This can be done by using restriction enzymes that cleave the coding sequence of a particular allele (e.g., the 158V allele) and that do not cleave the other allele (e.g., the 158F allele, or vice versa). Where such allele-specific restriction enzyme sites are not present naturally in the sequence, they may be introduced therein artificially, by amplifying the nucleic acid with allele-specific amplification primers containing such a site in their sequence. Upon amplification, determining the presence of an allele may be carried out by analyzing the digestion products, for instance by electrophoresis. This technique also allows to discriminate subjects that are homozygous or heterozygous for the selected allele.

Examples of allele-specific amplification primers include for instance SEQ ID NO:3. SEQ ID NO:3 introduces the first 3 nucleotides of the NlaIII site (5'-CATG-3'). Cleavage occurs after G. This primer comprises 11 bases that do not hybridise with FCGR3A, that extend the primer in order to facilitate electrophoretic analysis of the amplification products) and 21 bases that hybridise to FCGR3A, except for nucleotide 31 (A) which creates the restriction site.

In a further particular embodiment, determining amino acid residue at position 158 of FcγRIIIa receptor comprises a step of hybridization of the FCGR3A receptor gene or RNA or a portion thereof comprising the nucleotides encoding amino acid residue 158, with a nucleic acid probe specific for the genotype Valine or Phenylalanine, and determining the presence or absence of hybrids.

It should be understood that the above methods can be used either alone or in various combinations. Furthermore, other techniques known to the skilled person may be used as well to determine the FCGR3A158 genotype, such as any method employing amplification (e.g. PCR), specific primers, specific probes, migration, etc., typically quantitative RT-PCR, LCR (Ligase Chain Reaction), TMA (Transcription Mediated Amplification), PCE (an enzyme amplified immunoassay) and bDNA (branched DNA signal amplification) assays.

In a preferred embodiment of this invention, determining amino acid residue at position 158 of FcγRIIIa receptor comprises:

Obtaining genomic DNA from a biological sample,
Amplifying the FcγRIIIa receptor gene or a portion thereof comprising the nucleotides encoding amino acid residue 158, and
determining amino acid residue at position 158 of said FcγRIIIa receptor gene.

Amplification can be accomplished with any specific technique such as PCR, including nested PCR, using specific primers as described above. In a most preferred embodiment, determining amino acid residue at position 158 is performed by allele-specific restriction enzyme digestion. In that case, the method comprises:

Obtaining genomic DNA from a biological sample,
Amplifying the FcγRIIa receptor gene or a portion thereof comprising the nucleotides encoding amino acid residue 158,
Introducing an allele-specific restriction site,
Digesting the nucleic acids with the enzyme specific for said restriction site and,
Analysing the digestion products, i.e., by electrophoresis, the presence of digestion products being indicative of the presence of the allele.

In an other particular embodiment, the genotype is determined by a method comprising: total (or messenger) RNA extraction from cell or biological sample or biological fluid in vitro or ex vivo, optionally cDNA synthesis, (PCR) amplification with FCGR3A-specific oligonucleotide primers, and analysis of PCR products.

The method of this invention may also comprise determining amino acid residue at position 158 of FcγRIIIa receptor directly by sequencing the FcγRIIIa receptor polypeptide or a portion thereof comprising amino acid residue 158 or by using reagents specific for each allele of the FcγRIIIa polypeptide. This can be determined by any suitable technique known to the skilled artisan, including by immunoassay (ELISA, EIA, RIA, etc.). This can be made using any affinity reagent specific for a FcγRIIIa158 polypeptide, more preferably any antibody or fragment or derivative thereof. In a particular embodiment, the FcγRIIIa158 polypeptide is detected with an anti-FcγRIIIa158 antibody (or a fragment thereof) that discriminates between FcγRIIIa158V and FcγRIIIa158F, more preferably a monoclonal antibody. The antibody (or affinity reagent) may be labelled by any suitable method (radioactivity, fluorescence, enzymatic, chemical, etc.). Alternatively, FcγRIIIa158 antibody immune complexes may be revealed (and/or quantified) using a second reagent (e.g., antibody), labelled, that binds to the anti-FcγRIIIa158 antibody, for instance.

The above methods are based on the genotyping of FCGR3A158 in a biological sample of the subject. The biological sample may be any sample containing a FCGR3A gene or corresponding polypeptide, particularly blood, bone marrow, lymph node or a fluid, particularly blood or urine, that contains a FCGR3A158 gene or polypeptide. Furthermore, because the FCGR3A 158 gene is generally present within the cells, tissues or fluids mentioned above, the method of this invention usually uses a sample treated to render the gene or polypeptide available for detection or analysis. Treatment may comprise any conventional fixation techniques, cell lysis (mechanical or chemical or physical), or any other conventional method used in immunohistology or biology, for instance.

The method is particularly suited to determine the response of a subject to an anti-tumor therapeutic antibody treatment. In this regard, in a particular embodiment, the subject has a tumor and the therapeutic antibody treatment aims at reducing the tumor burden, particularly at depleting the tumor cells. More preferably, the tumor is a lymphoma, such as more preferably a B lymphoma, particularly a NHL. As indicated above, the antibody is preferably an IgG1 or an IgG3, particularly an anti-CD20 IgG1 or IgG3, further preferably a humanized antibody, for instance rituximab.

The invention also relates to a bispecific antibody, wherein said bispecific antibody specifically binds CD16 and a tumor antigen, for instance a CD20 antigen. The invention also encompasses pharmaceutical compositions comprising such a bispecific antibody and a pharmaceutically acceptable excipient or adjuvant.

Further aspects and advantages of this invention will be disclosed in the following examples, which should be regarded as illustrative and not limiting the scope of this application.

FIGURE LEGENDS

FIG. 1: Adjusted KAPLAN-MEIER estimates of progression-free survival after rituximab treatment according to FcγR3a-158V/F genotype (p=0.05).

Figure 2:
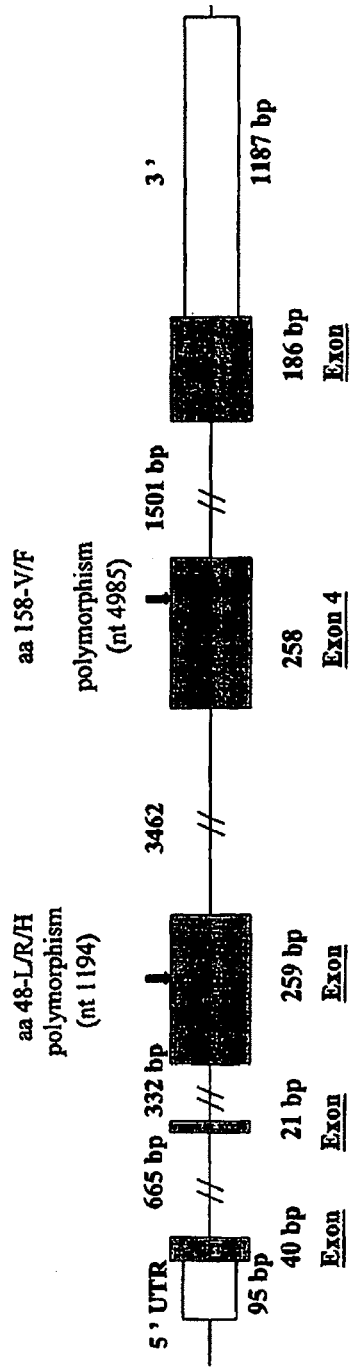

FIG. 2: Genetic organization of the human FCGR3A gene

FIG. 3: Amino acid sequences of human FcγRIIIa158F (SEQ ID NO:7)

FIG. 4A-H: Nucleic acid sequence of human FCGR3A158F (SEQ ID NO:8)

MATERIALS AND METHODS

Patients and Treatment

Clinical trial design, eligibility criteria and end-point assessment have been previously reported.[5] In brief, patients were eligible for inclusion in this study if they had previously untreated follicular CD20 positive NHL according to the REAL classification.[26] Patients were required to present with stage II to IV disease according to Ann-Arbor classification and at least one measurable disease site. All patients were required to have low tumor burden according to the GELF criteria.[27] A total of four 375 mg/m² doses of rituximab (Roche, Neuilly, France) were administered by intravenous infusion (days 1, 8, 15, 22). The management of infusion and adverse events has already been reported.[5] The study protocol was approved by an ethics committee, and all patients gave their informed consent.

Monitoring and Endpoints

Baseline evaluation included clinical examination, chest X-ray, computed tomography (CT) of the chest, abdomen and pelvis, and unilateral bone marrow biopsy. Response was assessed by an independent panel of radiologists who reviewed all the CT scans of the included patients. The primary efficacy endpoint was the objective response rate, i.e. the proportion of patients achieving either complete remission (CR), unconfirmed CR (CRu) or partial response (PR) according to the criteria recently proposed by an international expert committee.[28] Clinical response was evaluated at days 50 and 78. Only the maximum response was taken into account and that assessment time point named M2. All patients were evaluated for progression at one year (M12). Patients in CR or CRu with disappearance of bone marrow infiltration at M2 and reappearance of lymphoma cells in bone marrow at M12 were considered "progressive"; patients in PR with negative bone marrow biopsy at M2 and positive biopsy at M12 were considered in PR.

Molecular analysis of BCL2-JH gene rearrangement was performed by PCR, as previously described,[5] on a lymph node obtained at diagnosis and on both peripheral blood and bone marrow at diagnosis, M2 and M12.

FCGR3A-158V/F Genotyping

Out of the 50 patients included in the clinical trial, one patient was excluded after histological review and DNA was not available for two other patients. Forty seven patients were therefore available for FCGR3A genotype analysis. All samples were analysed in the same laboratory and DNA was extracted using standard procedures including precautions to avoid cross-contamination. DNA was isolated from peripheral blood (n=43), bone marrow (n=3) or lymph node (n=1). Genotyping of FCGR3A-158V/F polymorphism was performed as described by Koene et al[22] with a nested PCR followed by an allele-specific restriction enzyme digestion. Briefly, two FCGR3A specific primers (5'-ATATTTACA-GAATGGCACAGG-3', SEQ ID NO:1; 5'-GACTTGGTAC-CCAGGTTGAA-3', SEQ ID NO:2) (Eurobio, Les Ulis, France) were used to amplify a 1.2 kb fragment containing the polymorphic site. The PCR assay was performed with 1.25 µg of genomic DNA, 200 ng of each primer, 200 µmol/L of each DNTP (MBI Fermentas, Vilnius, Lithuania) and 1 U of Taq DNA polymerase (Promega, Charbonnière, France) as recommended by the manufacturer. This first PCR consisted in 10 min at 95° C., then 35 cycles (each consisting in 3 steps at 95° C. for 1 min, 57° C. for 1.5 min, 72° C. for 1.5 min) and 8 min at 72° C. to achieve complete extension. The second PCR used primers (5'-ATCAGATTCGATCCTACTTCTG-CAGGGGGCAT-3' SEQ ID NO:3; 5'-ACGTGCTGAGCT-TGAGTGATGGTGATGTTCAC-3' SEQ ID NO:4) (Eurobio) amplifying a 94 bp fragment and creating a NlaIII restriction site only in the FCGR3A-158V allele. This nested PCR was performed with 1 µL of the amplified DNA, 150 ng of each primer, 200 µmol/L of each dNTP and 1 U of Taq DNA polymerase. The first cycle consisted in 5 min at 95° C. then 35 cycles (each consisting in 3 steps at 95° C. for 1 min, 64° C. for 1 min, 72° C. for 1 min) and 9.5 min at 72° C. to complete extension. The amplified DNA (10 µL) was then digested with 10 U of NlaIII (New England Biolabs, Hitchin, England) for 12 h at 37° C. and separated by electrophoresis on a 8% polyacrylamide gel. After staining with ethidium bromide, DNA bands were visualized with UV light. For homozygous FCGR3A-158F patients, only one undigested band (94 bp) was visible. Three bands (94 bp, 61 bp and 33 bp) were seen in heterozygous individuals whereas for homozygous FCGR3A-158V patients, only two digested bands (61 bp and 33 bp) were obtained.

FCGR2A-131H/R Genotyping

Genotyping of FCGR2A-131H/R was done by PCR followed by an allele-specific restriction enzyme digestion according to Liang et al[28]. The sense primer (5'-GGAAAATCCCAGAAATTCTCGC-3' SEQ ID NO:5) (Eurobio) has been modified to create a BstUI restriction site in case of R allele whereas the antisense primer (5'-CAACAGC-CTGACTACCTATTACGCGGG-3' SEQ ID NO:6) (Eurobio) has been modified to carry a second BstUI restriction site that served as an internal control. PCR amplification was performed in a 50 µL reaction with 1.25 µg genomic DNA, 170 ng of each primer, 200 µmol/L of each dNTP, 0.5 U of Taq DNA polymerase, and the manufacturer's buffer. The first cycle consisted of 3 minutes at 94° C. followed by 35 cycles (each consisting in 3 steps at 94° C. for 15 seconds, 55° C. for 30 seconds, 72° C. for 40 seconds) and 7 min at 72° C. to complete extension. The amplified DNA (7 µL) were then digested with 20 U of BstUI (New England Biolabs) for 12 h at 60° C. Further analysis was performed as described for FCGR3A genotyping. The FCGR2A-131H and -131R alleles were visualized as a 337 bp and 316 bp DNA fragments, respectively.

Statistical Analysis

Clinical and biological characteristics as well as clinical and molecular responses of the patients in the different genotypic groups were compared using a Chi-squared test or by Fisher's exact test when appropriated. A logistic regression analysis including: sex, age (> or ≦60 years), number of extra-nodal sites involved (≧ or <2), bone marrow involvement, BCL2-JH rearrangement status at diagnosis and FCGR3A genotype was used to identify independent prognostic variables influencing clinical and molecular responses. Progression-free survival was calculated according to the method of Kaplan and Meier[29] and was measured from the start of treatment until progression/relapse or death. Comparison of the progression-free survival by FCGR3A genotype was performed using the log-rank test. P<0.05 was considered as statistically significant.

Results

Clinical Response

Out of the 49 patients tested for the FCGR3A-158V/F polymorphism, 10 (20%) and 17 (35%) were homozygous for FCGR3A-158V and FCGR3A-158F, respectively, and 22 (45%) were heterozygous. The three groups were not different in terms of sex, disease stage, bone marrow involvement, number of extra-nodal sites involved or presence of BCL2-JH rearrangement in peripheral blood and bone marrow at diagnosis (Table 1). No difference was found when homozygous FCGR3A-158V patients were compared with FCGR3A-158F carriers (FCGR3A-158F homozygous and heterozygous patients) or when homozygous FCGR3A-158F patients were compared with FCGR3A-158V carriers (FCGR3A-158V homozygous and heterozygous patients). The objective response rate at M2 was 100% (CR+CRu=40%), 70% (CR+CRu=29%) and 64% (CR+CRu=18%) in FCGR3A-158V homozygous, FCGR3A-158F homozygous and heterozygous patients respectively (P=0.09). A significant difference in objective response rate was observed between FCGR3A-158V homozygous patients and FCGR3A-158F carriers with 67% (CR+CRu=23%) objective response rate for this latter group (relative risk=1.5; 95% CI, 1.2-1.9; P=0.03) (Table 2). No difference was observed between FCGR3A-158F homozygous patients and FCGR3A-158V carriers. At M12, the objective response rate was 90% (CR+CRu=70%), 59% (CR+CRu=35%) and 45% (CR+CRu=32%) in FCGR3A-158V homozygous, FCGR3A-158F homozygous and heterozygous patients respectively (P=0.06). The difference in objective response rate was still present one year after treatment between FCGR3A-158V homozygous group and FCGR3A-158F carriers with 51% (CR+CRu=33%) objective response rate for this latter group (relative risk=1.7; 95% CI, 1.2-2.5; P=0.03). The logistic regression analysis showed that the homozygous FCGR3A-158V genotype was the only predictive factor for clinical response both at M2 (P=0.02) and at M12 (P=0.01). The progression-free survival at 3 years (median follow-up: 35 months; 31-41)(FIG. 1) was 56% in FCGR3A-158V homozygous patients and 35% in FCGR3A-158F carriers (ns). Out of the 45 patients analyzed for FCGR2A-131H/R polymorphism, 9 (20%) and 13 (29%) were homozygous for FCGR2A-131R and FCGR2A-131H, respectively, while 23 (51%) were heterozygous. There was no difference in the characteristics at inclusion or clinical response to rituximab treatment for these three groups or for homozygous FCGR2A-131H patients and FCGR2A-131R carriers, or for homozygous FCGR2A-131R patients and FCGR2A-131H carriers (data not shown).

Molecular Response

At diagnosis, BCL2-JH rearrangement was detected in both peripheral blood and in bone marrow in 30 (64%) patients, enabling further follow-up. Twenty-five patients (six FCGR3A-158V homozygous patients and 19 FCGR3A-158F carriers) and 23 patients (six FCGR3A-158V homozygous patients and 17 FCGR3A-158F carriers) were analysed for BCL2-JH rearrangement in both peripheral blood and bone marrow at M2 and at M12 (Table 3). At M2, a cleaning of BCL2-JH rearrangement was observed in 3/6 of the FCGR3A-158V homozygous patients and in 5/19 of the FCGR3A-158F carriers (ns). In contrast, the rate of BCL2-JH rearrangement cleaning at M12 was higher (5/6) in the FCGR3A-158V homozygous patients than in the FCGR3A-158F carriers (5/17) (relative risk=2.8; 95% CI, 1.26.4; P=0.03). The logistic regression analysis showed that the FCGR3A-158V homozygous genotype was the only factor associated with a greater probability of exhibiting BCL2-JH rearrangement cleaning at M12 (P=0.04). The single homozygous FCGR3A-158V patient still presenting with BCL2-JH rearrangement in peripheral blood and bone marrow at M12 was in CR 23 months after rituximab treatment. In contrast, the molecular responses at M2 and M12 were not influenced by the FCGR2A-131H/R polymorphism (data not shown).

Discussion

Because of the increasing use of rituximab in B cell lymphoproliferative malignancies, enhanced understanding of treatment failures and of the mode of action of rituximab is required. In this regard, we genotyped FCGR3A in follicular NHL patients with well-defined clinical and laboratory characteristics and treated with rituximab alone.[5] In particular, all the patients included in this study had a low tumor burden NHL and a molecular analysis of BCL2-JH at diagnosis and during follow-up. The FCGR3A allele frequencies in this population were similar to those of a general caucasian population.[23,24] Our results show an association between the FCGR3A genotype and the response to rituximab. Indeed, homozygous FCGR3A-158V patients, who account for one fifth of the population, had a greater probability of experiencing clinical response, with 100% and 90% objective response rates at M2 and M12, respectively. Moreover, five of the six FCGR3A-158V homozygous patients analysed for BCL2-JH rearrangement showed molecular response at M12, compared to 5 of the 17 FCGR3A-158F carriers. FCGR3A-158V homozygosity was the only factor associated with the clinical and molecular responses. However, these higher clinical and molecular responses were still unsufficient to significantly improve the progression-free survival in homozygous FCGR3A-158V patients.

This is the first report of an easily assessable genetic predictive factor for both clinical and molecular responses to rituximab. However, the genetic association does not demonstrate the mode of action of rituximab involves FcγRIIIa. The association observed between FCGR3A genotype and response to rituximab might be due to another genetic polymorphism in linkage disequilibrium. Those polymorphisms could be located in FCGR3A itself like the triallelic FCGR3A-48L/H/R polymorphism[31] or in other FcγR-coding genes, since FCGR3A is located on the long arm of chromosome 1, which includes the three FCGR2 genes and FCGR3B.[32] A linkage disequilibrium has been reported between FCGR2A and FCGR3B.[33] However, the fact that FCGR2A-131H/R polymorphism was not associated with a better response to rituximab strongly supports the fact that a gene very close to FCGR3A or FCGR3A itself is directly involved.

Several in vitro studies argue in favor of direct involvement of FCGR3A-158V/F polymorphism. First, Koene et al[23] have shown that the previously reported differences in IgG binding among the three FcγRIIIa-48L/H/R isoforms[31] are a consequence of the linked FcγRIIIa-158V/F polymorphism and several teams have demonstrated that NK cells from individuals homozygous for the FCGR3A-158V allotype have a higher affinity for human complexed IgG1 and are more cytotoxic towards IgG1-sensitized targets.[23,24,34] Our present results establish that FCGR3A-158V homozygous patients have a better response to rituximab, which is probably due to a better in vivo binding of that chimeric human IgG1 to FcγRIIIa. Secondly, NK cell- and macrophage-mediated ADCC is one of the mechanisms triggered by anti-CD20 antibodies in vitro[8,11,12] as well as in murine models in vivo,[17-19] and rituximab-mediated apoptosis is amplified by FcγR-expressing cells.[15,16] Out of all FcγR, FcγRIIIa is the only receptor shared by NK cells and macrophages. We thus postulate that FCGR3A-158V patients show a better response to rituximab because they have better ADCC activity against lymphoma cells. The fact that more than 50% of the FCGR3A-158F carriers nonetheless present a clinical response to rituximab could be explained by lower, but still sufficient, ADCC activity or, more likely, by other mechanisms operating in vivo such as complement-dependent cytotoxicity, complement-dependent cell-mediated cytotoxicity[11,13,14] and/or apoptosis.[15,16] ADCC could then be viewed as an additional mechanism in the response to rituximab that is particularly effective in FCGR3A-158V homozygous patients.

The in vitro studies suggest a "gene-dose" effect with a level of IgG1 binding to NK cells from FCGR3A heterozygous donors intermediate between that observed with NK cells from FCGR3A-158V and FCGR3A-158F homozygotes[23]. However, the clinical response of heterozygous patients appears similar to that of FCGR3A-158F homozygous patients. Further studies with larger groups of patients will be required to conclude against a "gene-dose" effect in vivo.

Since FcγRIIIa is strongly associated with a better response to rituximab, it needs to be taken into account in the development of new drugs targetting the CD20 antigen. For example, it may be possible to use engineered rituximab to treat FCGR3A-158F-carrier patients with B cell lymphomas. Indeed, by modifying various residues in the IgG1 lower hinge region, Shields et al have recently obtained IgG1 mutants which bind more strongly to FcγRIIIa-158F than native IgG1[34].

Taken together, these results allow to set up new therapeutic strategies against B lymphoproliferative disorders based upon prior determination of the patients FCGR3A genotype. Since this polymorphism has the same distribution in various ethnic population, including blacks and Japanese, such a strategy may be applied worldwide.[23,35,36] Furthermore, such a pharmacogenetic approach may also be applied to other intact humanized IgG1 antibodies used in the treatment of B cell malignancies, such as Campath-1H, or those used in the treatment of other malignancies, such as trastuzumab (Herceptin®). Even more generally, this approach may apply to other intact (humanized) therapeutic (IgG1) antibodies developed to deplete target cells.

REFERENCES

1. Maloney D G, Liles T M, Czerwinski D K, et al.: Phase I clinical trial using escalating single-dose infusion of chimeric anti-CD20 monoclonal antibody (IDEC-C2B8) in patients with recurrent B-cell lymphoma Blood. 1994; 84:2457-2466.
2. McLaughlin P, Grillo-Lopez A J, Link B K, et al.: Rituximab chimeric anti-CD20 monoclonal antibody therapy for relapsed indolent lymphoma: half of patients respond to a four-dose treatment program. J Clin Oncol. 1998; 16:2825-2833.
3. Maloney D G, Grillo-Lopez A J, White C A, et al.: IDEC-C2B8 (Rituximab) anti-CD20 monoclonal antibody therapy in patients with relapsed low-grade non-Hodgkin's lymphoma. Blood. 1997; 90:2188-2195.
4. Hainsworth J D, Burris H A, 3rd, Morrissey L H, et al.: Rituximab monoclonal antibody as initial systemic therapy for patients with low-grade non-Hodgkin lymphoma. Blood. 2000; 95:3052-3056.
5. Colombat P, Salles G, Brousse N, et al.: Rituximab (anti-CD20 monoclonal antibody) as first-line therapy of follicular lymphoma patients with low tumor burden: clinical and molecular evaluation. Blood. 2001; 97:101-106.
6. Coiffier B, Haioun C, Ketterer N, et al.: Rituximab (anti-CD20 monoclonal antibody) for the treatment of patients with relapsing or refractory aggressive lymphoma: a multicenter phase II study. Blood. 1998; 92:1927-1932.
7. Foran J M, Rohatiner A Z, Cunningham D, et al.: European phase II study of rituximab (chimeric anti-CD20 monoclonal antibody) for patients with newly diagnosed mantle-cell lymphoma and previously treated mantle-cell lymphoma, immunocytoma, and small B-cell lymphocytic lymphoma. J Clin Oncol. 2000; 18:317-324.
8. Anderson D R, Grillo-Lopez A, Vams C, Chambers K S, Hanna N: Targeted anticancer therapy using rituximab, a chimaeric anti-CD20 antibody (ODEC-C2B8) in the treatment of non-Hodgkin's B-cell lymphoma. Biochem Soc Trans. 1997; 25:705-708.
9. Vosej, Link B, Grossbard M, et al.: Phase II study of rituximab in combination with CHOP chemotherapy in patients with preiously untreated intermediate or high-grade non-Hodgkin's lymphoma (NHL). Ann Oncol. 1999; 10:58.
10. Berinstein N L, Grillo-Lopez A J, White C A, et al.: Association of serum Rituximab (IDEC-C2B8) concentration and anti-tumor response in the treatment of recurrent low-grade or follicular non-Hodgkin's lymphoma. Ann Oncol. 1998; 9:995-1001.
11. Hariunpaa A, Junnikkala S, Meri S: Rituximab (anti-CD20) therapy of B-cell lymphomas: direct complement killing is superior to cellular effector mechanisms. Scand J Immunol. 2000; 51:634-641.
12. Reff M E, Carner K, Chambers K S, et al.: Depletion of B cells in vivo by a chimeric mouse human monoclonal antibody to CD20. Blood. 1994; 83:435-445.
13. Idusogie E E, Presta L G, Gazzano-Santoro H, et al.: Mapping of the C1q binding site on rituxan, a chimeric antibody with a human IgG1 Fc. J Immunol. 2000; 164:4178-4184.
14. Golay J, Zaffaroni L, Vaccari T, et al.: Biologic response of B lymphoma cells to anti-CD20 monoclonal antibody rituximab in vitro: CD55 and CD59 regulate complement-mediated cell lysis. Blood. 2000; 95:3900-3908.
15. Shan D, Ledbetter J A, Press O W: Apoptosis of malignant human B cells by ligation of CD20 with monoclonal antibodies. Blood. 1998; 91:1644-1652.
16. Shan D, Ledbetter J A, Press O W: Signaling events involved in anti-CD20-induced apoptosis of malignant human B cells. Cancer Immunol Immunother. 2000; 48:673-683.
17. Hooijberg E, Sein J J, van den Berk P C, et al.: Eradication of large human B cell tumors in nude mice with unconjugated CD20 monoclonal antibodies and interleukin 2. Cancer Res. 1995; 55:2627-2634.
18. Funakoshi S, Longo D L, Murphy W J: Differential in vitro and in vivo antitumor effects mediated by anti-CD40 and anti-CD20 monoclonal antibodies against human B-cell lymphomas. J Immunother Emphasis Tumor Immunol. 1996; 19:93-101.
19. Clynes R A, Towers T L, Presta L G, Ravetch J V: Inhibitory Fc receptors modulate in vivo cytoxicity against tumor targets. Nat Med. 2000; 6:443-446.
20. Fijen C A, Bredius R G, Kuijper E J, et al.: The role of Fcγ receptor polymorphisms and C3 in the immune defence against *Neisseria meningitidis* in complement-deficient individuals. Clin Exp Immunol. 2000; 120:338-345.
21. Dijstelbloem H M, Scheepers R H, Oost W W, et al.: Fcγ receptor polymorphisms in Wegener's granulomatosis: risk factors for disease relapse. Arthritis Rheum. 1999; 42:1823-1827.
22. Myhr K M, Raknes G, Nyland H, Vedeler C: Immunoglobulin G Fc-receptor (FcγR) IIA and IIIB polymorphisms related to disability in MS. Neurology. 1999; 52:1771-1776.
23. Koene H R, Kleijer M, Algra J, Roos D, von dem Borne A E, de Haas M: FcγRIIIa-158V/F polymorphism influences the binding of IgG by natural killer cell FcγRIIIa, independently of the FcγRIIIa-48L/R/H phenotype. Blood. 1997; 90:1109-1114.
24. Wu J, Edberg J C, Redecha P B, et al.: A novel polymorphism of FcγRIIIa (CD16) alters receptor function and predisposes to autoimmune disease. J Clin Invest. 1997; 100:1059-1070.
25. Sondermann P, Huber R, Oosthuizen V, Jacob U: The 3.2-A crystal structure of the human IgG1 Fc fragment-FcγRIII complex. Nature. 2000; 406:267-273.

26. Harris N L, Jaffe E S, Stein H, et al.: A revised European-American classification of lymphoid neoplasms: a proposal from the International Lymphoma Study Group. Blood. 1994; 84:1361-1392.
27. Brice P, Bastion Y, Lepage E, et al.: Comparison in low-tumor-burden follicular lymphomas between an initial no-treatment policy, prednimustine, or interferon alfa: a randomized study from the Groupe d'Etude des Lymphomes Folliculaires. Groupe d'Etude des Lymphomes de l'Adulte. J Clin Oncol. 1997; 15:1110-1117.
28. Cheson B D, Horning S J, Coiffier B, et al.: Report of an international workshop to standardize response criteria for non-Hodgkin's lymphomas. NCI Sponsored International Working. J Clin Oncol. 1999; 17:1244.
29. Jiang X M, Arepally G, Poncz M, McKenzie S E: Rapid detection of the FcγRIIA-H/R 131 ligand-binding polymorphism using an allel-specific restriction enzyme digestion (ASRED). J Immunol Methods. 1996; 199:55-59.
30. Kaplan E, Meier P: Nonparametric estimation from incomplete observations. J Am Stat Assoc. 1958; 53:457-481.
31. de Haas M, Koene H R, Kleijer M, et al.: A triallelic Fcγ receptor type IIIA polymorphism influences the binding of human IgG by NK cell FcγRIIIa J Immunol. 1996; 156: 3948-3955.
32. Peltz G A, Grundy H O, Lebo R V, Yssel H, Barsh G S, Moore K W: Human FcγRIII: cloning, expression, and identification of the chromosomal locus of two Fc receptors for IgG. Proc Natl Acad Sci U S A. 1989; 86:1013-1017.
33. Schnackenberg L, Flesch B K, Neppert J: Linkage disequilibria between Duffy blood groups, FcγIIa and FcγIIIb allotypes. Exp Clin Immunogenet. 1997; 14:235-242.
34. Shields R L, Namenuk A K, Hong K, et al.: High resolution mapping of the binding site on human IgG1 for FcγRI, FcγRII, FcγRIII, and FcRn and design of IgG1 variants with improved binding to the FcγR. J Biol Chem. 2001; 276:6591-6604.
35. Leppers-van de Straat F G, van der Pol W, Jansen M D, et al.: A novel PCR-based method for direct Fcγ receptor IIIa (CD16) allotyping. J Immunol Methods. 2000; 242:127-132.
36. Lehrnbecher T, Foster C B, Zhu S, et al.: Variant genotypes of the low-affinty Fcγ receptors in two control populations and a review of low-affinity Fcγ receptor polymorphisms in control and disease populations. Blood. 1999; 94:4220-4232.

TABLE 1

CHARACTERISTICS OF PATIENTS ACCORDING TO THE FCGR3A-158V/F POLYMORPHISM.

|  | FCGR3A-158VV | FCGR3A-158VF | FCGR3A-158FF | p* |
|---|---|---|---|---|
| n (%) | 10 (20%) | 22 (45%) | 17 (35%) |  |
| Sex |  |  |  |  |
| M | 3 | 12 | 10 | ns |
| F | 7 | 10 | 7 |  |
| Disease stage |  |  |  |  |
| II–III | 3 | 6 | 6 | ns |
| IV | 7 | 16 | 11 |  |
| Bone marrow involvement |  |  |  |  |
| yes | 7 | 16 | 9 | ns |
| no | 3 | 6 | 8 |  |
| Extra-nodal sites involved |  |  |  |  |
| <2 | 8 | 20 | 13 | ns |
| ≧2 | 2 | 2 | 4 |  |
| BCL2-JH rearrangement in peripheral blood | 8 | 12 | 11 | ns |
| BCL2-JH rearrangement in bone marrow | 7 | 12 | 11 | ns |

*Satistical comparisons of the three groups of homozygous FCGR3A-158V patients vs FCGR3A-158F carriers and of homozygous FCGR3A-158F patients against FCGR3A-158V carriers.

TABLE 2

CLINICAL RESPONSE TO RITUXIMAB BY FCGR3A-158V/F POLYMORPHISM.

|  | FCGR3A-158VV | FCGR3A-158F carriers | p* |
|---|---|---|---|
| Clinical response at M2 |  |  |  |
| Objective response | 10 (100%) | 26 (67%) | 0.03 |
| complete remission | 3 | 7 |  |
| complete remission unconfirmed | 1 | 2 |  |
| partial response | 6 | 17 |  |
| No response | 0 (0%) | 13 (33%) |  |
| no change | 0 | 10 |  |
| progressive disease | 0 | 3 |  |
| Clinical response at M12 |  |  |  |
| Objective response | 9 (90%) | 20 (51%) | 0.03 |
| complete remission | 6 | 11 |  |
| complete remission unconfirmed | 1 | 2 |  |
| partial response | 2 | 7 |  |
| No response | 1 (10%) | 19 (49%) |  |
| no change | 0 | 2 |  |
| progressive disease | 1 | 17 |  |

*Satistical comparison of homozygous FCGR3A-158V patients against FCGR3A-158F carriers. Data concerning the three genotype subgroups are given in the text.

TABLE 3

MOLECULAR RESPONSE TO RITUXIMAB AT M2 AND AT M12 BY THE FCGR3A-158V/F POLYMORPHISM.

|  | FCGR3A-158VV | FCGR3A-158F carriers | p |
|---|---|---|---|
| Molecular response at M2 |  |  | ns |
| Cleaning of BCL2-JH rearrangement | 3 | 5 |  |
| Persistent BCL2-JH rearrangement | 3 | 14 |  |
| Molecular response at M12 |  |  | 0.03 |
| Cleaning of BCL2-JH rearrangement | 5 | 5 |  |
| Persistent BCL2-JH rearrangement | 1 | 12 |  |

The invention claimed is:

1. A method of predicting the responsiveness of a human follicular CD20 positive non-Hodgkin's lymphoma (NHL) patient to treatment with rituximab comprising:
   a) determining the identity of an amino acid residue at position 158 of the mature FcγRIIIa receptor of said human follicular CD20 positive non-Hodgkin's lymphoma (NHL) patient comprising obtaining a biological sample from a human follicular CD20 positive NHL patient and isolating and sequencing FcγRIIIa receptor polypeptides, or portions thereof containing an amino acid residue at position 158 of the mature form of the FcγRIIIa receptor from said biological sample to determine the amino acid residue at position 158 of said FcγRIIIa receptor polypeptides, or contacting antibody reagents specific for each allele of the FcγRIIIa receptor with said biological sample to determine the amino acid residue at position 158 present of said FcγRIIIa receptor; and
   b) identifying the amino acid residue at position 158 of the mature FcγRIIIa receptor as a valine (V) or phenylalanine (F), the presence of a homozygous (V/V) at position 158 of the FcγRIIIa receptor polypeptide being predictive of better responsiveness of said patient to treatment of follicular CD20 positive NHL with rituximab and the presence of a heterozygous (F/V) or a homozygous (F/F) at position 158 being predictive of a lower responsiveness of said patient to the treatment of follicular CD20 positive NHL with rituximab.

2. The method according to claim 1, wherein said determining the identity of an amino acid residue at position 158 of the mature FcγRIIIa receptor comprises sequencing FcγRIIIa receptor polypeptides or portions thereof comprising the amino acid residue at position 158 of the mature form of the FcγRIIIa receptor.

3. The method according to claim 1, wherein said determining the identity of an amino acid residue at position 158 of the mature FcγRIIIa receptor comprises contacting antibody reagents specific for each allele of the FcγRIIIa receptor with said biological sample to determine the amino acid residue at position 158 of the FcγRIIIa receptor present in said biological sample obtained from said patient.

4. A method of selecting a human patient that is more likely to respond to treatment of follicular CD20 positive non-Hodgkin's lymphoma (NHL) with rituximab comprising:
   a) identifying the amino acid at position 158 of the mature FcγRIIIa receptor comprising obtaining a biological sample from said human patient and sequencing FcγRIIIa receptor polypeptides, or portions thereof containing an amino acid residue at position 158 of the mature form of the FcγRIIIa receptor from said biological sample or contacting antibody reagents specific for each allele of the FcγRIIIa receptor with said biological sample to determine the amino acid residue at position 158 present in said biological sample obtained from said human patient; and
   b) selecting a human patient that is homozygous for (V/V) at position 158 of the mature form of the FcγRIIIa receptor polypeptide as being a patient that is more likely to respond to treatment of follicular CD20 positive non-Hodgkin's lymphoma (NHL) with rituximab than a human patient that is heterozygous (F/V) or homozygous (F/F) at position 158 of the mature form of the FcγRIIIa receptor polypeptide.

5. The method according to claim 4, wherein said identifying the amino acid at position 158 of the mature FcγRIIIa receptor comprises sequencing FcγRIIIa receptor polypeptides or portions thereof comprising the amino acid residue at position 158 of the mature form of the FcγRIIIa receptor.

6. The method according to claim 4, wherein said identifying the amino acid at position 158 of the mature FcγRIIIa receptor comprises contacting antibody reagents specific for each allele of the FcγRIIIa receptor with said biological sample to determine the amino acid residue at position 158 present in the biological sample obtained from said human patient.

7. A method of predicting the responsiveness of a human follicular CD20 positive non-Hodgkin's lymphoma (NHL) patient to treatment with rituximab comprising:
   a) determining the identity of an amino acid residue at position 158 of the mature FcγRIIIa receptor of said human follicular CD20 positive non-Hodgkin's lymphoma (NHL) patient comprising obtaining a biological sample from a human follicular CD20 positive NHL patient and carrying out a method selected from the group consisting of:
      (i) isolating and sequencing the gene of the human patient that encodes the FcγRIIIa receptor, or a portion of the gene that encodes an amino acid at position 158 of the mature form of the FcγRIIIa receptor in said biological sample, to determine the identity of the amino acid residue at position 158 of the mature FcγRIIIa receptor;
      ii) isolating and hybridizing FcγRIIIa receptor encoding RNA or a portion thereof in said biological sample, said portion comprising those nucleotides encoding amino acid residue 158 of the mature form of the FcγRIIIa receptor, with a nucleic acid probe specific for the nucleotides encoding valine or phenylalanine to determine the amino acid residue present at position 158 of the mature FcγRIIIa receptor;
      (iii) A) obtaining genomic DNA from said biological sample;
         B) amplifying the FcγRIIIa receptor gene or a portion thereof in said biological sample to form amplification products comprising the nucleotides encoding the amino acid residue at position 158 of the mature form of the FcγRIIIa receptor; and
         C) sequencing the amplification products of step B) and determining the identity of the amino acid residue at position 158 of said mature form of the FcγRIIIa receptor; and
      (iv) A) obtaining genomic DNA from said biological sample;
         B) amplifying the FcγRIIIa receptor gene or a portion thereof in said biological sample to form amplification products comprising nucleotides encoding the amino acid at position 158 of the mature form of the FcγRIIIa receptor;
         C) digesting the amplification products of step B) with an enzyme that cleaves at a valine codon to form digestion products; and
         D) analyzing the digestion products of step C) to identify the presence of digestion products indicative of the presence of a valine at position 158 of the mature form of the FcγRIIIa receptor; and
   b) the presence of a homozygous valine at position 158 of the mature FcγRIIIa receptor encoded in the genomic DNA from said biological sample or the presence of a nucleotide sequence encoding a valine at position 158 of the mature FcγRIIIa receptor in RNA from said biological sample being predictive of better responsiveness of said patient to treatment of follicular CD20 positive NHL with rituximab in comparison to a human patient that is homozygous (F/F) at position 158 of the mature form of the FcγRIIIa receptor.

8. The method according to claim 7, wherein said determining the identity of an amino acid residue at position 158 of the mature FcγRIIIa receptor comprises:
   a) obtaining genomic DNA from said biological sample;
   b) amplifying the FcγRIIIa receptor gene or a portion thereof in said biological sample to form amplification products comprising nucleotides encoding the amino acid residue at position 158 of the mature form of the FcγRIIIa receptor; and
   c) sequencing the amplification products of step b) and determining the identity of the amino acid residue at position 158 of said FcγRIIIa receptor.

9. The method according to claim 7, wherein said determining the identity of an amino acid residue at position 158 of the mature FcγRIIIa receptor comprises:
   a) obtaining genomic DNA from said biological sample;
   b) amplifying the FcγRIIIa receptor gene or a portion thereof in said biological sample to form amplification products comprising nucleotides encoding the amino acid at position 158 of the mature form of the FcγRIIIa receptor;
   c) digesting the amplification products of step b) with an enzyme that cleaves at a valine codon to form digestion products; and
   d) analyzing the digestion products of step c) to identify the presence of digestion products indicative of the presence of valine at position 158 of the mature form of the FcγRIIIa receptor.

10. The method according to claim 8, wherein said amplifying is performed by polymerase chain reaction (PCR), RT-PCR or nested PCR.

11. The method according to claim 9, wherein said amplifying is performed by polymerase chain reaction (PCR), RT-PCR or nested PCR.

12. The method according to claim 10, wherein said amplifying is performed by nested PCR and primers comprising SEQ ID NOs: 1, 2, 3 and 4 are used in said nested PCR process.

13. The method according to claim 11, wherein said amplifying is performed by nested PCR and primers comprising SEQ ID NOs: 1, 2, 3 and 4 are used in said nested PCR process.

14. The method according to claim 7, wherein said determining the identity of an amino acid residue at position 158 of the mature FcγRIIIa receptor comprises hybridization of the FcγRIIIa receptor encoding RNA or a portion thereof in said biological sample, said portion comprising those nucleotides encoding amino acid residue 158 of the mature form of the FcγRIIIa receptor, with a nucleic acid probe specific for the nucleotides encoding valine or phenylalanine.

15. A method of selecting a human patient that is more likely to respond to treatment of follicular CD20 positive non-Hodgkin's lymphoma (NHL) with rituximab comprising:
   a) determining the identity of an amino acid residue at position 158 of the mature FcγRIIIa receptor of a human patient comprising a method selected from the group consisting of:
      (i) obtaining a biological sample from said human patient containing genomic DNA and sequencing the gene of the human patient that encodes the FcγRIIIa receptor, or a portion of the gene that encodes an amino acid at position 158 of the mature form of the FcγRIIIa receptor, to determine the identity of the amino acid residue at position 158 of the mature FcγRIIIa receptor;
      (ii) hybridizing the FcγRIIIa receptor encoding RNA or a portion thereof present in a biological sample from said human patient, said portion comprising those nucleotides encoding amino acid residue 158 of the mature form of the FcγRIIIa receptor, with a nucleic acid probe specific for the nucleotides encoding valine or phenylalanine;
      (iii) A) obtaining genomic DNA from a biological sample from said human patient;
         B) amplifying the FcγRIIIa receptor gene or a portion thereof in said biological sample to form amplification products comprising the nucleotides encoding the amino acid residue at position 158 of the mature form of the FcγRIIIa receptor; and
         C) sequencing the amplification products of step B) and determining the identity of the amino acid residue at position 158 of said FcγRIIIa receptor; and
      (iv) A) obtaining genomic DNA from a biological sample of said human patient;
         B) amplifying the FcγRIIIa receptor gene or a portion thereof in said biological sample to form amplification products comprising nucleotides encoding the amino acid at position 158 of the mature form of the FcγRIIIa receptor;
         C) digesting the amplification products of step B) with an enzyme that cleaves at a valine codon to form digestion products; and
         D) analyzing the digestion products of step C) for the presence of digestion products indicative of the presence of a valine at position 158 of the FcγRIIIa receptor; and
   b) selecting a human patient that has a valine at position 158 of the mature form of the FcγRIIIa receptor encoded in the genomic DNA from said biological sample or in the nucleotide sequence of the RNA encoding the mature form of the FcγRIIIa receptor polypeptide present in said biological sample as being more likely to respond to treatment of follicular CD20 positive non-Hodgkin's lymphoma (NHL) with rituximab than a human patient without said valine.

16. The method according to claim 15, wherein said determining the identity of an amino acid residue at position 158 of the mature FcγRIIIa receptor comprises:
   a) obtaining genomic DNA from said biological sample;
   b) amplifying the FcγRIIIa receptor gene or a portion thereof in said biological sample to form amplification products comprising the nucleotides encoding the amino acid residue at position 158 of the mature form of the FcγRIIIa receptor; and
   c) sequencing the amplification products of step b) and determining the identity of the amino acid residue at position 158 of said FcγRIIIa receptor.

17. The method according to claim 15, wherein said determining the identity of an amino acid residue at position 158 of the mature FcγRIIIa receptor comprises: a) obtaining genomic DNA from said biological sample; b) amplifying the FcγRIIIa receptor gene or a portion thereof in said biological sample to form amplification products comprising nucleotides encoding the amino acid at position 158 of the mature form of the FcγRIIIa receptor; c) digesting the amplification products of step b) with an enzyme specific for a restriction site to form digestion products; and d) analyzing the digestion products of step c) for the presence of digestion products indicative of the presence of a valine at position 158 of the FcγRIIIa receptor.

18. The method according to claim 16, wherein said amplifying is performed by polymerase chain reaction (PCR), RT-PCR or nested PCR.

19. The method according to claim 17, wherein said amplifying is performed by polymerase chain reaction (PCR), RT-PCR or nested PCR.

20. The method according to claim 18, wherein said amplifying is performed by nested PCR and primers comprising SEQ ID NOs: 1, 2, 3 and 4 are used in said nested PCR process.

21. The method according to claim 19, wherein said amplifying is performed by nested PCR and primers comprising at least one of SEQ ID NOs: 1, 2, 3 and 4 are used in said nested PCR process.

22. The method according to claim 15, wherein said determining the identity of an amino acid residue at position 158 of the mature FcγRIIIa receptor comprises hybridization of the FcγRIIIa receptor encoding RNA or a portion thereof present in a biological sample from said human patient, said portion comprising those nucleotides encoding amino acid residue 158 of the mature form of the FcγRIIIa receptor, with a nucleic acid probe specific for the nucleotides encoding valine or phenylalanine.

23. A method of predicting the responsiveness of a human subject having follicular CD20 positive non-Hodgkins lymphoma (NHL) to treatment with rituximab, comprising: a) identifying the amino acid at position 158 of the mature FcγRIIIa receptor in a biological sample from a human subject having follicular CD20 positive NHL patient as a valine (V) or a phenylalanine (F); and b) predicting better responsiveness of the human subject to treatment with rituximab based on the identification of the human subject having a homozygous (V/V) at position 158 of the FcγRIIIa receptor, or predicting lower responsiveness of the human subject to treatment with rituximab based on the identification of the human subject having a heterozygous (F/V) or a homozygous (F/F) at position 158 of the FcγRIIIa receptor.

24. A method for treating a human patient with follicular CD20 positive non-Hodgkin's lymphoma (NHL) that is more likely to respond to treatment with rituximab comprising: administering rituximab to a human subject identified as being homozygous for valine (V/V) at position 158 of the mature form of the FcγRIIIa receptor, such that the human subject is more likely to respond to treatment with rituximab as compared to a human subject identified as being heterozygous for valine (FN) or homozygous for phenylalanine (F/F) at position 158 of the mature form of the FcγRIIIa receptor.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: FCGR3A
      specific primer.

<400> SEQUENCE: 1
atatttacag aatggcacag g                                              21

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: FCGR3A
      specific primer.

<400> SEQUENCE: 2
gacttggtac ccaggttgaa                                                20

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence:
      Amplification primer.

<400> SEQUENCE: 3
atcagattcg atcctacttc tgcaggggggc at                                  32

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence:
      Amplification primer.

<400> SEQUENCE: 4
acgtgctgag cttgagtgat ggtgatgttc ac                                   32

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence:
      Amplification sense primer.

<400> SEQUENCE: 5
ggaaaatccc agaaattctc gc                                             22

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence:
      Amplification antisens primer.

<400> SEQUENCE: 6
caacagcctg actacctatt acgcggg         27

<210> SEQ ID NO 7
<211> LENGTH: 254
<212> TYPE: PRT
<213> ORGANISM: Artificial Sequence
<220> FEATURE:
<223> OTHER INFORMATION: Description of Artificial Sequence:
      Amino acid sequence of human FCGR3A158F.

<400> SEQUENCE: 7

```
Met Trp Gln Leu Leu Pro Thr Ala Leu Leu Leu Val Ser Ala
  1               5                  10                  15

Gly Met Arg Thr Glu Asp Leu Pro Lys Ala Val Val Phe Leu Glu Pro
                 20                  25                  30

Gln Trp Tyr Arg Val Leu Glu Lys Asp Ser Val Thr Leu Lys Cys Gln
             35                  40                  45

Gly Ala Tyr Ser Pro Glu Asp Asn Ser Thr Gln Trp Phe His Asn Glu
         50                  55                  60

Ser Leu Ile Ser Ser Gln Ala Ser Ser Tyr Phe Ile Asp Ala Ala Thr
 65                  70                  75                  80

Val Asp Asp Ser Gly Glu Tyr Arg Cys Gln Thr Asn Leu Ser Thr Leu
                 85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 8
<211> LENGTH: 22685
<212> TYPE: DNA
<213> ORGANISM: Artificial Sequence
<220> FEATURE:
<223> OTHER INFORMATION: Description of Artificial Sequence: Nucleic
      acid sequence of human FCGR3A158F.

<400> SEQUENCE: 8
cagcctggct gacacagtga gacctcatct ctaaaaaaaa aagcaagcag aatattttct   60
taaaaggcaa ttatattcct tcttggccag gcccagtggc tcacacctgt aatcccagca  120
ctttgggagg ccgagatggg tggatcacct gaggtcagga gttcgagacc agcctggcca  180

-continued

```
acatggcgaa aacccgtgtc tactaaaaat acaaaaatta gctgggcatg ggggcatatg      240
cctgtaatcc cagctacttg ggaggctgag acaggagaat cgcttgtacc cgggaggcag      300
agattgcagt gagccgagat catgccactg cactccagcc ttggcgacag agtgaggctt      360
tgtctaaaaa aaaaaaggta ttttttgcct ctctgttggt accaattgtt aaattctttg      420
tggaccactg atgcttacca aaaaaaaaaa aaaaaaagt gggggcatca tatttcctct       480
agttgacatt aagacacagt aatttagcca gaggagatct tagcaaacat acagtccaca      540
ctccactttc tcatttcatg attgtagaga ctgagatcta gacaatttaa tcggtggtca      600
ccctgggtga catagctagg tctagagctc ctggtctcca ggtcagcatt tctttcttct      660
tcattaaatg tcaagtttcc tcccctgttc attattagct ccttccagaa agagagtttc      720
ttatctttt agtaggtact cagtaaatac caaggtattc actaggatgc ctttggatga       780
aggtaacaag ccctgactta aattggctta acagcaggg aaatttactt gaaattgtaa       840
gaaatctggg ttggttgcgt tagaagctca gtgatgtcac caagaccata ttctatccct      900
ccactctgtc ctccttggct atttggcatt gacctcagac tggctgcctt caaaatctta      960
ggttttgcca gcagaaccta ggacaaaatg agcccttgtt catgtacagt gggagagaga     1020
gatcatctct cccaaacatg gcactcccct ctaccagatt ggcccctattt aggacaaagt    1080
tccgtcttct cccacttaac caataaaagc caggggaatg ctacaccctg agtggcttag     1140
atcagtcaag atccacctct gcatatgagg gtgattcctg aatagaatca aggttatatt     1200
agaagggagg gagagggatg gatatcaggc tagtacatca tattctattt gttgagttaa     1260
ctgagtcata gcaattgttg agttggaaaa aactcagaac ctactgtgga ttcaagttca     1320
agaaatcatt ctttcctaca tacaacagca ttgctctgta gccctgagct aagagagcat     1380
cacgaaatac agtcttcttg ctgtttataa tcgtaagcaa actcttggac ctgggagggg     1440
atgaatggaa aatgtctgtc tgacttgctt ctttctagtt agtaccaact acctcccttc     1500
ttcctgtgat tgttcttaga ataggataaa aaatcttccc ttccctagat cttacagtct     1560
ccccttcccc caggcctttc tattttttcag gattttactc taatcacacc accgaagaat    1620
caagaaatct ttaaagtgta ttagagtagc tagttgtggc agcactaaaa cacggctgca     1680
aattctttga cactctctcc atcaagaaat gaggcctaca tcctctaccc ttgaatctgg     1740
gtgggcttat aacttctggt gattagacta cagcagaaag agaagctgta tagcttccta     1800
aatgttataa agtcttaagg atagctgcca gcaagacctt aggacaaaat gagcccttgt     1860
tcacgtccag tgggagagag agagagagac cctctctccc aaatatggca atcctctcta    1920
cctataacat ttacataaat gttataggtt aaacgttcca caacaaacta agtactattt     1980
aacatcaaga ggaaaagag acaggagaaa gggttaataa gcctgttgat gaggatctaa      2040
gaagaacaaa ggaggcctgg tttgggcctg gctacccgtt ggtcttgcaa agaagagtct     2100
gaggtggcag agccttcagt ggcagatgcc aaattatcat catgagtgac tgcaagacag     2160
tgtcagctaa gatagccatt tcaagctgct gaaggccttc tcttttagtc gtggagtcct     2220
gtgataagaa ctgaaagttg gaagagtgtg cttgtctgtg gccttatttg gtcggatgca     2280
gtctttatca ttttttaattt gtttcttaga acatttatc ttgttggcca aatgccctac     2340
gaaatataaa atggagtctt tttctaagat ggagttagtt atgtcaaggg tcctttatac     2400
agtcttcatc cttttttcctg gcatacaact cctaaaatcc ttagaatctc caaagtgatg    2460
tcttttggtg tgctaatgag gtaactgatg gctggcagct cttaggtagc ttcataacag     2520
gggctgggca caagaaagat catggcaagg tcagaggatt ggggctttca gctccaccct    2580
```

```
ccaaactccc tctgggaagt ggagaggggc tgaaggttga attgatcacc aatagccaat    2640
gacttaatta atcattccta agtaataaag ctcccataaa aacccaaaag gacagggttt    2700
ggagatcctc cagagagccg aacacagaga ggttcttgga gggtagtgca ccagagggca    2760
tggaagctcc aagccccttc ccacaggtct tgccctatgt actctttact tgtgtccttt    2820
gtaatattct ttatcacaaa ctgataaatg taaatgtttc cctgagtact gagagccact    2880
ctagcaaatt aattgaaccc aagatgcagg tggtgggaac ccccatttat aactggttgg    2940
tcaaaagcac aggtaaaaca acctgggggct tcatcctgga gtatcagaag tgtcttgtga    3000
gactgagccc ttcacttgtg tcacctgatg ctatttccag ttagatagtg ttggaattca    3060
attgaatttg agcagaagtc ccaatcccca gacctgtagt tgtcagtgac ctcttaggaa    3120
ctgggctgca cagcaggaag tgaggggcag gtggggagca aagctttatc tgtatttaca    3180
gtagatcccc atggctcaca tcaccgcctg agctcctcct cctatcagat cagctgtggc    3240
attaaattat cacaggagca tgaaccctat tgtgaagtac gcatgcaagg gatctaggtt    3300
gcattctcct tatgagaatc taatgcctga tgacctggca ttgtctccca tcacccctaga    3360 tgggactgtc tagttgcaag aaaacaagct cggggctccc cctgattcta cattatggta    3420
agttgtataa ttacttcatt aaatattaca ctgtaataat aatagaaatg aagtgcacaa    3480
taaatgtaat gcacttgaat catcctgaaa ccatccccca ccccctacc cctgtccgag    3540 gaaaaattgt cttccatgaa gccaatccct ggtgccaaaa attttggaga ccactggatt    3600
agaagacacc cagttggtgc ccactgctga attgcttgct tgcttgcttg cttgcttgcc    3660
agtggagaga aatccccaca tatctgttgt cagaaatgtg ttgtgagagc atagtgggag    3720
gaactgagtt tgttttttct acagttacag caataggtaa ctggaattca actgctggac    3780
tataccaaag actgccaggc cagcctacct ttctcacagc cttcttgact acctgtcttg    3840
gatgagctca ctgaaagccc acataccttc attctagcat ttcctcagtc tggttgagct    3900
gctttggagg taatacaggt tgtaggactt ccctccactc ctgctcagga ccgttttcag    3960
caggctaatc agacagcagt tggcactgag tacaactgga gaaatgttat cagcactgaa    4020
gactgctcca gctacaaatg cacagcgacc cacctcagct ggacctttgg cattgcttgg    4080
caatccttac aactgtttgg aattcttggt aattcttgta catacaaaca gtcggctcct    4140
tctcccatgc accacaatgg ccattctcaa ctctggtgtt ctcaaacccc caccacaact    4200 gttaccccact ctttctcgac aagtgtctttt gactcctcct taaccaagaa aatcaggacc    4260
agcagatgtg gatggtcact caacatctga aaatggatttt gcatatgtac cccctcagct    4320
cctgccttca gctcagagcg agaggtaatc cgtatccagt tcacagccaa ctccctgtcc    4380
atgtcccatt cccatctcct caggacccac acttgcttct ctaggtgttc cgtccctgtt    4440
aggcatccaa cttctcccac cctgctggct tcttcccaaa gacctataac caagctcgta    4500
tctttcactt aaaagaaaac aaaaactccc attctcttgt aactacccttt gcagaattgt    4560 gtctgaaaca gtgagagaga tctaacttaa ttgactccat cttgcttcta acctccaagc    4620
tgtctttcct cattcttggg cataggctga actaactttg ggagaaactt agtttatagt    4680
ttgtggttta aagcaaagat gataacagcc ctttcccagg gcagacctcc ttttttttctg    4740 aagactagat tgtctttgta ggactaacat tagccacaag attggaaatt atggtttagg    4800
aatcatgcag gtggaggcta caagattctg acccttccta agcactgatc ctaagatcgg    4860
tgcttgagat attttgcaga ccctgcactt gatggatcac ctggcaacac ccagatcaat    4920
```

```
aaactggctc atctgatctt gtggtgccca cccaggaact gactcagaac aagaagacag    4980
cttcaacttc ctgtgatttc atccctgacc aatcaacact cctggctcac tggcttcccc    5040
tccaccaacc aagttgtcct taaaaactct gctccccgaa tgctctggaa gactgatttg    5100
agtaataata aaactccagt ctctggctca gtcagctctg catgaattac tctttctcta    5160
ttgcaattcc cctgtcttga tgaatcagct ctgtctagtt accatcctcc acttctcctt    5220
tcttattgtg tcacttaggg ctctgggtta taaacaactt tatcagaatc cagatctttt    5280
aagtagagga aaaagattta ttggatggaa actagaggag gtgagcccat cccactgctg    5340
tgatgactgg gacccaacca tctccctctc ctagaagtga atctcccttg tgagtaaaca    5400
agtgtcactt attcaggatt catctcagaa gagactctaa tgggccaaac ctcagttata    5460
tgcctgtcct ctgtctgcct gtatcagtta gctagcactt ttataacaaa gtaccacaga    5520
ctgggtggct taaacaacaa aaatgtattt tcttacagtt cttgaggctg caagtccaag    5580
atcaaggtgt tgacagggtt ggtttctttt aattttttt ttaaaaattt tattttagat    5640
ttaggggtat gcgtgcaggt ttgctacata ggtaaactcc tatcacgggg gtttgttgca    5700
cacattattt catcacccat gtactaagcc tagttactca atagttattt tttccgatcc    5760
tctccctctt cctaccctcc accctcaagt aggccccagt gtgtctgttg ttcttccttt    5820
gagtccatag ggtggtttc ttctgaggcc tctctccttg gcttgtaggt gtccatcttc    5880
tccctgtatg ggtctgtgtc ccaactaaca aggacatcag tcatattgga ctagagccca    5940
cctaatgatt ttattttaac ttaattacct ctttaaaggc tctatatcca catatagtca    6000
catcctgagg tataggggggt tccacatgtg gacttcaaca tatgaactgg gagagacaaa    6060
atttagtcct taatagtgcc ccaaagtggg gaaaaggaag atctggaccc tcgggtttcc    6120
atagtagaaa gcaatcactg cttttctatta agtactcaca gtggggcttc tccagaaaga    6180
atgatatgct aataagaagg ggaggaggaa gtgatcctgg acagccagat gatatgtgca    6240
ctattccttc ataatggaga ttctgaagag gagaagcact tgactaaaca cttttttcatt    6300 cctactccgt cttcaaccaa aagctgtcaa acttctgttt ctcagcccca gcccctgaaa    6360
ttgctcagga aaaggtcatt aatagttcct tgattgccat atttcaatca aactcttgtt    6420
tgaattcttt tctacaacat taatactgtt actgttgact actccttcct tgaagatctg    6480
ttcccactaa acttccttgt tccctcctct tcagcccctc ctatacaaac tcctttgtca    6540 gctattttc ctgtgcacgc ttcaaaaatg tttgcatgtc aagtttctgt cattgactct    6600
ctcctcttct cctctccctc tcaatccctc cttccttttcc ctcactgttt cccttttaatt    6660 ctctctcaat actcttacag tttcagagat cttatcctta ctttatctta acctaggatc    6720
tctggatgga ttcaaataga gcttcttaaa ttaaaggaaa cataatgtgt atatttgcat    6780 ccttctcttgg gagaaggccc aaaggtttt atcagaggtt tgaaacctca accgtgttgg    6840
tgcctcctaa attgtgtctt ttgtcaagac ctgtcttctg agttccaggg ccatgtgtct    6900
cactgcctac tggaaatctt cacctgaaac cttcacagct acctcaaact caataacatc    6960
aaaagctgaa atcattgtct ctccctccca aagcctgctc atcttcccat tttcttttg     7020 tccatgaaag ctactgccat cctccttatc acccaaatta gaaatccgag catcacccag    7080
acctctcccc cttcatcacc cctcagccaa tcactcacca agtcttgtcc atccttcctt    7140
cctaacttct ctcctggatg cttccattgc atatccactt tttaaacaga gtggctcttg    7200
tctcaactag actgttgaaa taatcttcca acttttccct ccaccttcca tctctctccc    7260
ctctaactca ttccttggac tgctgtcaga gtacttttca taaaatataa aacagatctt    7320
```

```
gtgattcccc agtctaaagc cttttatta gttcccatta cctttagaa taaaatatgt    7380 actgttcatc ctgacacaca aaactcttcg tgataaatac taattgagtg cctagtatgt    7440
gcctgccctt gtgctaaatg ttgagggtac aggggtaaac aaggtgaaca gcttccctgc    7500
tctccaagac ctttcagtcc acaaatgcaa tgagtttaca gaggagaagc acaagctcct    7560
aaaggagttg gggtggggtt ggggtcaga acctaattta gaaaattgag gaaggtctca    7620
acctcccatc ttgcatttac aatagtaatc agcaggtgtg gtaccaaata tggaaccaac    7680
aattttatct gcattatctc atttaagcca tgagtgccat tattgttagc ctcacttac    7740 agataaggaa actgagggct agaaggttaa ataagtggca gagttgggat ttcctccaga    7800
ttcctgtgag acccagacat cttaatcctt tggaacctg tgcttctcct ttgtagtact    7860
cactacactt gtggaactac atccaactac acttgtggaa ctacagccag ctctgcaaac    7920 atgcagtct acttcactcc aagtctttgc tcatgctgct cctcttgcct ggaatgccta    7980
tttctctcaa aaatcttcct gctgaatatt ttgcgatcta attaaagtgt tctctcttcc    8040
atgtacactc ctccctcaga tagaattagc cactgtcttc tttgtgcata cacagcattt    8100
cataaatact gtcacagtcc ctctagcact tcaaatactt atctgatgtt ctcccctaa    8160 gaaactgtaa gtcctagagg atgacaatca actgaattcc atagtcagaa acttctgctg    8220
tgcctggcct tccaatgaga aaaggagaga agaggagggg aaggaagaaa aagggaagga    8280
gaagaaagaa aagcaaacat gaagataaac acttcaatat atgatatccc aagaccatct    8340
acccttttgt aaaaattttg cttttttttt ttccccccca agagtcaggg tctcactctg    8400
tcgcccaggc tagagtgcag tgccatgaac ataactcact gtagcctcta actccggggc    8460
tcaagcaatc ctcctgcctc agcctcctgg gtagctggga ctacaggcat gcaccaccac    8520
atctggctat tattattatt actatattag tagagatggg gtctttctat gttgcctagg    8580
ctggtctcaa attcctggcc tcaagcaatt cttccacctc acattggcct tccaaagtgc    8640
tgggattaca ataagccacc ataggccaaa attttgcatt ttatccatta ctgtaaaatt    8700 aaccettaga aatccaacaa cactcaattt gagaattgtt caacaaccac ttaatgaaaa    8760 cccctgaaa gcttcccatc ctgttgcagt ccctttctct cctcctgtgc tctctcctct    8820
tcttcctatc tagcccaccc ttttggcagc taagaattcc tccctccatt ggagagccac    8880
agaccaaaga ggagtcaaat aagaaaataa gacctcaaag aaggaaaaca aagtgaaggc    8940
cttgcatcag aagtcacgtg gcagaaagcc acctggatat ctgaaaagaa gaagaattg    9000 agggatatcc gctttttgcc tcagagacca tccttagccc tgaaggcttt gtttctgctt    9060
taggtttccc agataagcat ccgaagtgct acagcaagga actttaagtt tccagatact    9120
tgtctggatt ttgcaaggcg tagatgagtc acttgagaag gagaactgga atggctgcct    9180
gggttcattt ccattgtcca atccaagggc ctgtggagaa gggctgctg caagactctg    9240 tgtgtggcgg ggggagggt gggtacgtgg atggcaatgg gaggatcaat taactccacc    9300
caggagccaa atgaaacaca caaataaaaa acaaaacctg agtagtggtt tttaggtcat    9360
tctggagtag aaagagcatt catttatagc aaaggttggc gggcacctgt gtcagcccct    9420
gcctccactc cacccctaac aagtatcagg tgcccacacg ggcctgctgc tcgcctcctg    9480
ggcttttcta agccaggtga gacctgtccc agatgtccac gaatccactg ggggagtggc    9540
actatcaagc agagtcatct gattttctgc ctgggacctg gaccattgtg agagtaacca    9600
acgtggggtt acggggagga atctggagag aagagaagag gttaacaacc ctcccacttc    9660
```

```
ctggccaccc ccctccacct tttctggtaa ggagccctgg agccccggct cctaggctga    9720
cagaccagcc cagatccagt ggcccggagg ggcctgagct aaatccgcag gacctgggta    9780
acacgaggaa ggtaaagagt tcctgtcctc gcccctcccc accccacct tttctgtgat     9840 cttttcagcc tttcgctggt gacttgttct tccagggccc atttctctac cctacctggg    9900
tttcttctaa cctggaaatc taatgatcaa atcacactaa aaagtcagta gctcctgtgg    9960
attacatatc ccaggagcat atagattttg aattttgaat tttgaaagaa attctgcgtg   10020
gagataatat tgaggcagag acactgctag tggtctgaag atttgaaagg accactttct   10080
gtgtgcaggc agggcctcag ctggagatag atgggtctgg gcgaggcagg agagtgacaa   10140
gttctgaggt gaaatgaagg aagccctcag agaatgctcc tcccaccttg aatctcatcc   10200
ccagggtctc actgtcccat tcttggtgct gggtggatcc aaatccagga gatggggcaa   10260
gcatcctggg atggctgagg gcacactctg gcagattctg tgtgtgtcct cagatgctca   10320
gccacagacc tttgagggag taaagggggc agacccaccc accttgcctc caggctcttt   10380
ccttcctggt cctgttctat ggtggggctc ccttgccaga cttcagactg agaagtcaga   10440
tgaagtttca agaaaaggaa attggtgggt gacagagatg ggtggagggg ctggggaaag   10500
gctgtttact tcctcctgtc tagtcggttt ggtcccttta gggctccgga tatctttggt   10560
gacttgtcca ctccagtgtg gcatcagggg ctggggaaag gctgtttact tcctcctgtc   10620
tagtcggttt ggtcccttta gggctccgga tatctttggt gacttgtcca ctccagtgtg   10680
gcatcatgtg gcagctgctc ctcccaactg ctctgctact tctaggtaag tcagggtctc   10740
cctggttgag ggagaagttt gagatgcctt gggttcagca gagacccctt ttcaggctac   10800
gaatgagact cccacgaagg gatgggaccc ctcaccacat ctatagctgt ggattgagct   10860
cctaggacaa gccaagatgg ggctagaaat gaggagaatg ctggttccaa ttggggcata   10920
ctcatgagtg aggccagtca cttcacccct ctgggtccca gaatcactct gtggaaccaa   10980
agagcttcga ctagatggtc cctagggtct gtctctttca gtttgacatt ccagggttct   11040
cctctatgat tttcaatttc taccctttct tgtggggata tgggttgagg ctctttctgt   11100
agcttggttc agggaaattc aacctgtacc cttaatttgt gagtttgcac agggagcaag   11160
gggtaaggga gcagtgttga aaatagggat ttgtgttgac agtggcgcaa gaggcatgaa   11220
cagtggagac cagagagcag gtagcaaggt ttccaccaga aacatcctga ttcttgggaa   11280
aattgggctc ctggggcaga ggagggcagg ggagttttaa actcactcta tgttctaatc   11340
actctgatct ctgcccctac tcaatatttg atttatcttt tttcttgcag tttcagctgg   11400
catgcggact ggtgagtcag cttcatggtc ttggattgac ccagtggggc acatatgggg   11460
acaaaggcca taagatattg ggaaatgctt gttgaatggg aaaatgctga tgtgggtta    11520 gcagggatag ttcctccaac acagcagaac ttggccctgt gcttctctgg ccagctttcc   11580
ttaagatact gaacaggcca aaaatggggc caagatgctc taagactgag ccaccaagca   11640
tgggtttgca atgagctcat tctggctttg aggctccctg ggaatggcag tgtagagcct   11700
gctcctctcc ctgtcctcac cccacattat cttggctcct cagaagatct cccaaaggct   11760
gtggtgttcc tggagcctca atggtacagg gtgctcgaga aggacagtgt gactctgaag   11820 tgccaggag cctactcccc tgaggacaat tccacacagt ggtttcacaa tgagagcctc    11880
atctcaagcc aggcctcgag ctacttcatt gacgctgcca cagtcgacga cagtggagag   11940
tacaggtgcc agacaaacct ctccaccctc agtgacccgg tgcagctaga agtccatatc   12000
ggtgagttga tgaaggggaa gaggaaaatc accaataaag ggtgaaacaa agggtcctga   12060
```

-continued

```
aatacttggt aagagccaga gatgatattc ttagagataa aagctaagat gagatgatgt    12120
gtggtcccac tgaatggtat cagagttgta gtcctagctc taagtaggtc ttgggcaaaa    12180
tgtcaaagcc tgtcagacag tagatatagg actgctgcat tgcacaattc caagaatccc    12240
catatggagt gcatacaatg tgaatgtgtc atgtgaaggt taggccatgg catagatgct    12300
caataatagt tatttatata tttattttca ttttttttaa ttttattttt tgagacagag    12360
tatcactctg tcacccaggc tggagtgcaa tgcggcaatc tcagctcact gcaacttctg    12420
cccccttggg ttgtagtgat tctcctgcct cagcctcccg agtagctgag attacaggca    12480
cccgccacca cgcccagcta attttttgtat ttttagtaga cagggtttt caccatgttg    12540 gtcagtctgg tctcaaactc ctgacctcag gtgattcacc agccttggct tcccaaagtg    12600
ctgggactac aggcgtgagc caccacacct ggccaataat atttattgaa taaattaatg    12660
aatttggtgt taggacctca atctccttct cgctctcaga catgtaatgc cctaagccac    12720
ctcccaaagc aatcctagtg gcctagcatc atatctttct gtctcctcat caatgctata    12780
ctcaaaccta taattaagca taaatttggt aatgtgatag ctcttccaat agaggcagat    12840
acatgttcag cctgcacatt aatcatgaca tgaaagttct tgtgtactat aacagaata    12900 tagacgtcag acacaggtag gagaaatatt ttgaaggcag aggtctttcc tggtgtccct    12960
acaatcttac cacataggct ggtccctgca gtgtcgccct gcaaacctaa ctctacttcc    13020
acggctgttc cattcataca atgtttatgg gtgaacaag ctttggggga agaagggcat    13080
aaggaggtgg atctgcaaga gagctccatg gaattgggcc tctgaaactg attttttgtgg    13140 ctctttggcc tctgacagta ccactcaact gacatggtct tcactctcca gagctacaag    13200
aagatatgtc catttctagc taggtaagag atgtccacct acaaccaaat aaaatggggg    13260
aattaccaag agaaagcaat agaaaaatca agtctaagag ttactagttt gccttgaact    13320
tggctctaga aactggcttt agaagtctag ccaatcaagg ctatattaaa ctgtgaccat    13380
gagaattagc ttcaccaggt aaacttctga gcatccttta atcctttagg acccatttca    13440
cttatgtcct cctctgagaa gcatttttta cttcttttt tgtttgtttg tttgtgtttg    13500
tttttgtttt tgttttgag acagagtctc tctctgtcac ccaagctgga gtgcagtggc    13560
gcaatcttgg ctcactgcaa cctccacctc ccggggttcaa gcaattctcc tgcctcagcc    13620
tcccaagtag ctgggactac aggtgcatgc caccacgccc ggctaatttt ttgtattttt    13680
agtagagaca gggtttcgca gcgttagcca ggatggtctt gatctcctga cttcatgatc    13740
tgcccacctc ggcctcccaa agtactagga ttacagatgt gagccaccgc gcccagcctg    13800 catttttac ttcttttcagg cagaatttct ttattccaat ctagtcagcc ccgcagtcct    13860
ttattcttag cctgttgtag cacttgtcat attgtattgt gattatttct gaatatttat    13920
gtttctatgt ctagactgta gattctttga ggctgagaac tatatgtccc atcatctggg    13980
tatctccagt ccacagtgtg tcatacatag tgagtgcttg atgaaatatc acttgaagga    14040
atatacatat ggacattcac tgggtccatg acaggataga ttcgaacaag aatgttcctc    14100
caaaggccac cagactatat actaaccatg actttatgct aataatgatt catctctctg    14160
ctgaaaaagt aagtggatag ataggcacat ggcttctttt gataaatgat atctcttaat    14220
aggtaatgaa gattactttc tgtttggcaa atctttgtgg tagagaatca tgaccaacac    14280
acgtcctacc aatttttgttt agcatcaggt agtagatttt ttaaattata gtaattcaag    14340
ctgagaatgt agatttaaaa aataaaaatta ttgtaaattt tgttttgttc ttattacaaa    14400
```

```
agtcatttgg ggtcaatttc aaaaatatat aaaagtaaac aggagaaatt taaaatgtcc    14460
ttcagtccca ctccttcaga gaaaacccct gttaatatgt aagtgcatat ccttctttt    14520 tctgtgcata atactttta aaatatttga agtattatgc ttttttaact taaaattgtc    14580
tcatgaatat tttcttatgc cattataata cttacctata acatcattat tttttaatta    14640
ttcaggccct ttcccgacca tgacctcatg ttctctcttt gtgaagtctg attacttggt    14700
gacatgatcg tgagaataag ctctggcgat ataagaattc cctctcttga aggccatgct    14760
cagtaaatta cttggtgaca tgatcgtgag aataagctct ggcgatacaa gaatttcctc    14820
tcttgaaggc catgctcagt aataaagttg gtctcaccga ggccctgtga caccttagaa    14880
accacgaatt gccaggctga gcaataccag tcccgccctt ccctccctg gtgtttacat    14940 tgagttctcc ttcacaattt ctgcagccac tccgtggcca ccgtcacctt attcctgact    15000
gccacaagag tctttcaata ttcctttgat tgcctattcc ttctgaaatc taccttttcc    15060
tctaataggg caattcatca ttttcaaatg caattttac tctgatctag aacttactgt    15120
gaatccttgt cacctgccac agcaaatcta agtctagcac ttaaggatcc tgcagatatg    15180
ctcatcgttg cttctcactt acctcattgc ttagtccctc tgctctaacc ctgtgtgttg    15240
atcacatgtg tgtgtgtccc tcttccccat tagacaaagg tcttggtatg acttcagttc    15300
tcttgcaggg ccccatcagc tcttcccaa agggagctat gcagggttga ctcccaatct    15360
ggctttccct tatgtctcag gatctgggtg gtacgtggcc ccttcacaaa gctctgcact    15420
gagagctgag gcctcccggg cctggggtgt ctgtgtcttt caggctggct gttgctccag    15480 gccctcggt gggtgttcaa ggaggaagac cctattcacc tgaggtgtca cagctggaag    15540
aacactgctc tgcataaggt cacatatta cagaatggca aaggcaggaa gtattttcat    15600
cataattctg acttctacat tccaaaagcc acactcaaag acagcggctc ctacttctgc    15660
agggggcttt ttgggagtaa aaatgtgtct tcagagactg tgaacatcac catcactcaa    15720
ggtgagacat gtgccaccct ggaatgccca gggacgcctg tgtgtggaac ctgcaatcac    15780
actgggaagt tgagttggga ggagattcct gattcttaca cgcacttctt catatgtggt    15840
tccctcctgg tgatcaccag gaggtcccca aaagtccctg attgcagggt aggtttgcag    15900
ctctgtttca gtccattctt ttggggtagc taggaggtgt cattcactct gcagcatgat    15960
ggcaggagca gaagccacat ctcctcccca ataaatacct ctgtcttttcc ttacgctaat    16020 cacacccacg gtgtcatatg ttcctatcgt gctggcctcc ttcttatcca agcctttttag    16080 ccacgatcca aactggcagg agcccctcat cccctcacag aaagagccca gaacctgggt    16140
tctggccctg cagctaatta accatctgac cagaggtgag ccacttagtc tctctgaacc    16200
ccaatttctt cttccgtaac aaaaataagc tgacatttat tgggcacctt tcagtgtgct    16260
agactctgtg ctaaacaatt ctttacatgc acctggtttg actatcacag tagaccttca    16320
caacatgaga taggtaatat tccattttac agatgaagta accgaggtgc aaaaataaat    16380
aaataagttt ccctaaggtc acatcaaaga cttcaaagcc tgtatattta accagtaagt    16440
aaaagatttg aacaagcact aatatccta tgatcccatta agtcatccac aaaacatctc    16500
taggttctgt agcaccagcc tccagaatca gagctctaga gtggtgtgcc tggactttcc    16560
agtttcacag aacttctatc tgtaactagc ccaagcacata aattgtaaac aatttgcatg    16620
tagaaaggca gcaaaacacc ttttgagatt ttgacactac aatgccataa tttgtacaaa    16680
aataatttca tgcacttta aactgaaagt aaatactccc aagtggttag ggaaagagag    16740
caaataaagc aaatggggta acatgtaaac aatgagtgga tctgggtaaa ggatatacga    16800
```

```
gattaaacta ttctggtcat tttttttta agtttggaaa tatatcaaaa tcaagagttt    16860
aaaaaattga aatgcaaaat caacaaattt gtcccagttt ctagaccata gcattgtctg    16920
acaatttctt aactgtcaca caaacccag cttacaacct aacttgttaa cgctccctgt    16980
cacatctctg tcaaacaagc aggagccttt gctcagtgtt tggtgagctg tcctctgctc    17040
agatagcact aagatcagga accaatggga ggaagcaata ctttccccca gacttcccca    17100
ccattcctac cacttgcctg ttggctgttg tcaaagactt tctactggtg acctcactgt    17160
ttgttccaaa tatctgcctt agtgactgtc attttttttc atctctccac ttctcctaat    17220
aggtttggca gtgtcaacca tctcatcatt cttccacct gggtaccaag tctctttctg    17280
cttggtgatg gtactccttt ttgcagtgga cacaggacta tatttctctg tgaagacaaa    17340
cattcgaagc tcaacaagag actggaagga ccataaattt aaatggagaa aggaccctca    17400
agacaaatga cccccatccc atgggggtaa taagagcagt agcagcagca tctctgaaca    17460
tttctctgga tttgcaaccc catcatcctc aggcctctct acaagcagca ggaaacatag    17520
aactcagagc cagatccctt atccaactct cgacttttcc ttggtctcca gtggaaggga    17580
aaagcccatg atcttcaagc agggaagccc cagtgagtag ctgcattcct agaaattgaa    17640
gtttcagagc tacacaaaca cttttctgt cccaaccgtt ccctcacagc aaagcaacaa    17700
tacaggctag ggatggtaat cctttaaaca tacaaaaatt gctcgtgtta taaattaccc    17760
agtttagagg ggaaaaaaaa acaattattc ctaaataaat ggataagtag aattaatggt    17820
tgaggcagga ccatacagag tgtgggaact gctggggatc tagggaattc agtgggacca    17880
atgaaagcat ggctgagaaa tagcaggtag tccaggatag tctaagggag gtgttcccat    17940
ctgagcccag ataagggt gtcttcctag aacattagcc gtagtggaat taacaggaaa    18000
tcatgagggt gacgtagaat tgagtcttcc aggggactct atcagaactg gaccatctcc    18060
aagtatataa cgatgagtcc tcttaatgct aggagtagaa aatggtccta ggaagggggac    18120 tgaggattgc ggtgggggt ggggtggaaa agaaagtaca gaacaaaccc tgtgtcactg    18180
tcccaagttg ctaagtgaac agaactatct cagcatcaga atgagaaagc ctgagaagaa    18240
agaaccaacc acaagcacac aggaaggaaa gcgcaggagg tgaaaatgct ttcttggcca    18300
gggtagtaag aattagaggt taatgcaggg actgtaaaac caccttttct gcttcaatat    18360
ctaattcctg tgtagctttg ttcattgcat ttattaaaca aatgttgtat aaccaatact    18420
aaatgtacta ctgagcttcg ctgagttaag ttatgaaact ttcaaatcct tcatcatgtc    18480
agttccaatg aggtggggat ggagaagaca attgttgctt atgaaagaaa gctttagctg    18540
tctctgtttt gtaagcttta agcgcaacat ttcttggttc caataaagca ttttacaaga    18600
tcttgcatgc tactcttaga tagaagatgg gaaaaccatg gtaataaaat atgaatgata    18660
aaattctttc ttcttcccctt tgtccaacat tgtaacagag attggtttgg attggtaaga    18720 aacacccct cctcccagca accatctcac cacaactcat ataaattagc cagcttgctt    18780
tccaaatctt gctgagacaa ttgggctaag gaggattctt atgggaagta tgggatagga    18840
gggtgaataa gcattagaga tcgttttaga gcattggggc agataggaga aggcacagct    18900
acacaggagg tagaggcctg ggcagaggta gagggtcagc ctgattgtat gaattatgag    18960
ctatatacca agacgattca agctagattg catacataaa tattacataa gattccgaca    19020
cgacacaggt gcatttggaa accttggaca ttcaactcac attatttac tacctacaat    19080 gtgcaagctt gagttcaggt gctgaagata ccagatgaac aacacaggt cattccctgg    19140
```

```
agaagcttta tttctagtga gaaaaacagt taaataggaa gagaatgaag aaagggctgc   19200
agaaaagagg cttgatttgg ggggtgtggt catgaaggat gagtaggagt tcgccaggca   19260
aagaagagaa gaaaagccca aggttcatag gcaaagattc aaaaaccaga gtgtgagttc   19320
aagaaagcag tttggttctg tgtcggtgag ggagaggaaa gagtttcagg gccagatcat   19380
gaagggcatt accttccaaa ctaaggagat cgtatcagac cctgcaatac attgagagag   19440
tttaagcaga ccaggtttgt accgtatagt attttagaag gattctctcg caactacttg   19500
atggatggac gggacaggag agttgaagac cagaagccaa atagggcagc aaggcaggat   19560
gcagtaaccc aaagggagca atgaggaagt aactggcggt gaggctggag aggaaggtgc   19620
ttaatcaaca aggtatttag gaggccgact ctccaagaat tggcagccag cagtacacgg   19680
cgtgactaag gaccaggttc cacacatagt gcccgttttc tgagttagga aatagaaagg   19740
caaggcaggt acaggtttgg tggaaagaca acaattcgt tttggtatta ttagtactta    19800
cttcctttgg tcagtaaatt ttcttaaagt gtcagtttcc ataacgtaat tgccgtggtt   19860
aagcagctaa gagttatcac tacaacccta gtcggaaaaa ccaaataccct caaaattacc   19920 cgtacagcac taaggcagaa gaggacattg ggaaccacac aacgcggagg tctgctacca   19980
gagctccctg cggttagcac cgcggctggt tttgagcgcc aaggcccag cgctcccagc    20040 ggatagcatc gcacgcagtt ttttcagtca aagtttcaaa aacccagggt tcacaaaatg   20100
cgacttccgt ccctgggtgg gatcgaacca ccaacctttc ggttaacagc cgaacgcgct   20160
aaccgattgc gccacagaga cgggcgttgg cgattttggc tgccaagtca cttcactgaa   20220 gaaaaatgc tcagcactca cgtctccaaa aaaattgagg ttgatttgaa accagtgaca     20280
caattagctt tccgtgcttc agggcgcggc tcatagccct gagcgaggca ggtcttttt   20340 ctgcgctagc acttgcctag atctggagca ggactcagct tccagcagaa gaggttgaga   20400
aaaggagagc agaagagaat gcaggaacga agggtcttcg gggaatccaa aatggatgct   20460
ctctgtgggt tcggggttc cgttgatttt ggtcagagaa gtacgacgat aagctttttt    20520
tgctgatgta gacaacttat gtatgcatgt gcacacgttt agtgctgact cataataagc   20580
ttattatcgt gagcattaaa aatatttcct ttcaggtcca atcacgtcca gcaaaatgtg   20640
atgtctaagt aagtgagttt tgtgttacaa aattagtctt caacccacgc tgttttgaaa   20700
ggtttctacc ggcatattag acatgcagac agaacacgga gcttaaaaag cctgtaacat   20760
tccaattaat ggtattcagc ttggaaataa aaaatatttt ttaaaaaatg cgtgcaactt   20820
aaggactttc atgctgacat atccagatcc aaatatctga ggacagagac ccctaattcc   20880
accaccatcg acctagggaa cctcgtcagt gctgggtcta aaaaggcttt ttttttttct   20940
ttaattcata tgtatatata ctttattcat atatatatat actttaagtt ctaggctaca   21000
tgtgcacaag gtgcaggttc gttacatata catgtgccat gttggtgtgc tgcacccatt   21060
aactcgtcat ctacattagg tgtttctcct aatgttatcc ctccctcctt ccccacccca   21120
cgacaggtcc cggtgtgtga tgttccctac catgcacacg tatgtttatt gtggaactat   21180
tcacaatagc aaagacttgg aaccaaccca atgtccatc aatgatagac tggattaaga    21240
aaatgtggca catatacact atggaatact atgcagccat aaaaaaggat gagttcatgt   21300
cctttgtagg gacatagatg aagctggaaa ccatcagtct gaacaaacta tcacaaggac   21360
agaaaatcag acaccgcatg ttctcactca taggtgggaa ttgaacaata agaacacttg   21420
gacgaaagcc attttctata ttgcccaaaa accagggtct ctccatagcc tccacacaga   21480
atctcctttc tttctgccct gccatcctct gtcatcagtg ggctccagtt taggagcagg   21540
```

-continued

```
tggaagtttt caatgatgtt cagtgaaatg agaagacatg caaacataga tatgtatatg    21600
cagaaattat atatgcatat atgtttatat gtacacagta tcatatgtat aataaataag    21660
taaataaata aataaatttg ccaaatgatc tttaaactag agtcatttat ttttttttatt    21720 aattttttttt tttgagatgg agtcttgctc tgtcgcccag gctggagtgc agtggcgcaa    21780
tcttggctca ctgcaacctc cacctcccac attcaagcaa ttctcctgtc tcagcctcct    21840
gagtagctga gattacagtc atgggccacc atgcccggct aattttttgta ttttttttttt    21900 ttttttttg agacagagtc tcgctgtcgc ccaggttgga gtgcagtggc gcgatctcgg    21960
ctcactgcag gctccgcccc cgggattca cgccattctc ctgcctcagc ctcctgagta    22020
gctgggacta caggcacctg ccacctcgcc cggctaattt ttttgtattt ttggtagaga    22080
tgggctttcg ctatgttggc caggctggtc tcaaactcct gacctcaggt gatcctcctg    22140
cctcagcctc ccaaactgct gggattacag gtgagagcca ctgtaccagg cctagagtca    22200
tttcttttat actttaaatt tttgtctctg ttctttttgct cagacctgtg gagctggcaa    22260
tatgggcaag tgtcatggac tgtctactgc caggaagctc cattgtcacc gacaggatca    22320
gaagtggcat ggtaaatggt acaagaaagc ccattcgggc acagtcctga agaccagcct    22380
ttttggaggt gcttctcatg caaagggaat tgggctggaa aaagtaggga ttggagccaa    22440
atagcccagc tctgccactg agaagtgtgc cagggccaag ctgatcatcc agcataagct    22500
agatgctgtg gtctccactg gcacagctga tcctcttgtt acaggatgga ggctgtgagg    22560
cagatgagag aacagcaaga aaatcacagc ctttgtacct gatgatgatt gcttgaattt    22620
tattgaaaaa aatgatgaag ttctgtatca ggggaaccag cacccaatat ttcaatgtag    22680
gttct                                                               22685
```

<210> SEQ ID NO 9
<211> LENGTH: 45
<212> TYPE: DNA
<213> ORGANISM: Artificial sequence
<220> FEATURE:
<223> OTHER INFORMATION: FCGR3A gene 158F allele
<220> FEATURE:
<221> NAME/KEY: exon
<222> LOCATION: (1)..(45)

<400> SEQUENCE: 9

```
tcc tac ttc tgc agg ggg ctt ttt ggg agt aaa aat gtg tct tca         45
Ser Tyr Phe Cys Arg Gly Leu Phe Gly Ser Lys Asn Val Ser Ser
1               5                   10                  15
```

<210> SEQ ID NO 10
<211> LENGTH: 45
<212> TYPE: DNA
<213> ORGANISM: Artificial sequence
<220> FEATURE:
<223> OTHER INFORMATION: FCGR3A gene 158v allele
<220> FEATURE:
<221> NAME/KEY: exon
<222> LOCATION: (1)..(45)

<400> SEQUENCE: 10

```
tcc tac ttc tgc agg ggg ctt gtt ggg agt aaa aat gtg tct tca         45
Ser Tyr Phe Cys Arg Gly Leu Val Gly Ser Lys Asn Val Ser Ser
1               5                   10                  15
```